United States Patent
Fey et al.

(10) Patent No.: US 9,328,066 B2
(45) Date of Patent: May 3, 2016

(54) CHIRAL SYNTHESIS OF N-{3,4-DIFLUORO-2-[(2-FLUORO-4-IODOPHENYL)AMINO]-6-METHOXYPHENYL}-1-[2,3-DIHYDROXY-PROPYL]CYCLOPROPANESULFONAMIDES

(75) Inventors: Peter Fey, Wuppertal (DE); Agathe Christine Mayer, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/122,568

(22) PCT Filed: May 24, 2012

(86) PCT No.: PCT/EP2012/059717
§ 371 (c)(1),
(2), (4) Date: Feb. 3, 2014

(87) PCT Pub. No.: WO2012/163799
PCT Pub. Date: Dec. 6, 2012

(65) Prior Publication Data
US 2014/0155637 A1    Jun. 5, 2014

(30) Foreign Application Priority Data
May 27, 2011 (EP) ..................................... 11167806

(51) Int. Cl.
| | | |
|---|---|---|
| C07C 211/43 | (2006.01) | |
| C07D 317/10 | (2006.01) | |
| C07C 303/38 | (2006.01) | |
| C07C 303/40 | (2006.01) | |
| C07C 309/71 | (2006.01) | |
| C07D 309/12 | (2006.01) | |
| C07D 317/18 | (2006.01) | |
| C07F 7/18 | (2006.01) | |
| C07D 303/34 | (2006.01) | |
| C07D 317/24 | (2006.01) | |

(52) U.S. Cl.
CPC ............. *C07C 303/38* (2013.01); *C07C 303/40* (2013.01); *C07C 309/71* (2013.01); *C07D 303/34* (2013.01); *C07D 309/12* (2013.01); *C07D 317/18* (2013.01); *C07D 317/24* (2013.01); *C07F 7/1856* (2013.01); *C07B 2200/07* (2013.01); *C07C 2101/02* (2013.01)

(58) Field of Classification Search
CPC ............................ C07C 211/43; C07D 317/10
USPC .................... 564/305, 307; 549/430, 453
See application file for complete search history.

(56) References Cited

U.S. PATENT DOCUMENTS

| | | | | |
|---|---|---|---|---|
| 8,513,443 | B2 * | 8/2013 | Maderna et al. | 549/453 |
| 8,884,058 | B2 * | 11/2014 | Maderna et al. | 564/80 |
| 2008/0058340 | A1 | 3/2008 | Maderna et al. | |

FOREIGN PATENT DOCUMENTS

| | | |
|---|---|---|
| WO | 2007025540 A2 | 3/2007 |
| WO | 2007121269 A1 | 10/2007 |
| WO | 2008024725 A1 | 2/2008 |
| WO | 2008025822 A1 | 3/2008 |
| WO | 2010145197 A1 | 12/2010 |
| WO | 2011009541 A1 | 1/2011 |

OTHER PUBLICATIONS

Blotny, G., "A new, mild preparation of sulfonyl chlorides," Tetrahedron Letters, 2003, 44:1499-1501.

(Continued)

*Primary Examiner* — Golam M M Shameem

(57) ABSTRACT

The present invention relates to a novel enantioselective method of preparing (S)- and (R)-enantiomers of N-{3,4-difluoro-2-[(2-fluoro-4-iodophenyl)amino]-6-5 methoxyphenyl}-1-[2,3-dihydroxy-propyl]cyclopropanesulfonamide, to novel intermediate compounds, and to the use of said novel intermediate compounds for the preparation of said (S)- and (R)-enantiomers of N-{3,4-difluoro-2-[(2-fluoro-4-iodophenyl)amino]-6-methoxyphenyl}-1-[2,3-dihydroxy-propyl]cyclopropanesulfonamide.

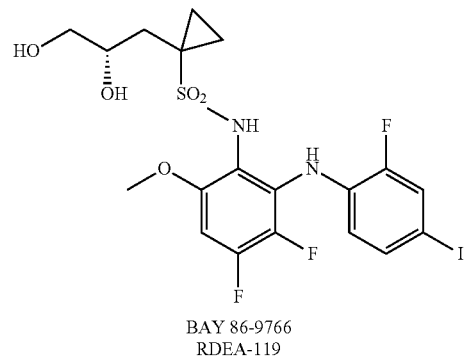

BAY 86-9766
RDEA-119

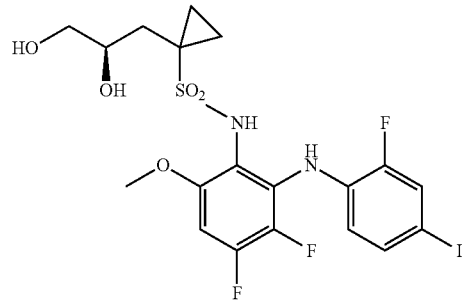

13 Claims, No Drawings

(56) References Cited

OTHER PUBLICATIONS

Fey et al., "Synthesis of BAY 86-9766/RDEA119 via Chiral Sulfonate Intermediates," IP.com Journal, May 30, 2011, 11(6A):41.
Fujita, S., "A Convenient Preparation of Aremesulfonyl Chlorides from the Sodium Sulfonates and Phosphoryl Chloride/Sulfolane," Synthesis, May 1982, 5:423-424.
Huang, et al., "Facile Synthesis of Sulfonyl Chlorides," Tetrahedron Letters, 1992, 33(19):2657-2660.
Iverson et al, "RDEA119/BAY 869766: A Potent, Selective, Allosteric Inhibitor of MEK1/2 for the Treatment of Cancer," Cancer Research, Sep. 1, 2009, 69(17):6839.

\* cited by examiner

CHIRAL SYNTHESIS OF N-{3,4-DIFLUORO-2-[(2-FLUORO-4-IODOPHENYL)AMINO]-6-METHOXYPHENYL}-1-[2,3-DIHYDROXY-PROPYL]CYCLOPROPANESULFONAMIDES

FIELD OF THE INVENTION

The present invention relates to a novel enantioselective method of preparing (S)- and (R)-enantiomers of N-{3,4-difluoro-2-[(2-fluoro-4-iodophenyl)amino]-6-methoxyphenyl}-1-[2,3-dihydroxy-propyl]cyclopropanesulfonamide, to novel intermediate compounds, and to the use of said novel intermediate compounds for the preparation of said (S)- and (R)-enantiomers of N-{3,4-difluoro-2-[(2-fluoro-4-iodophenyl)amino]-6-methoxyphenyl}-1-[2,3-dihydroxy-propyl]cyclopropanesulfonamide:

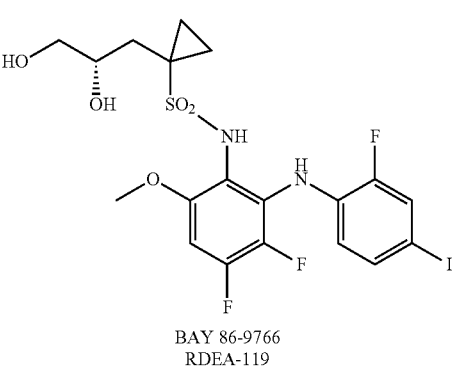

BAY 86-9766
RDEA-119

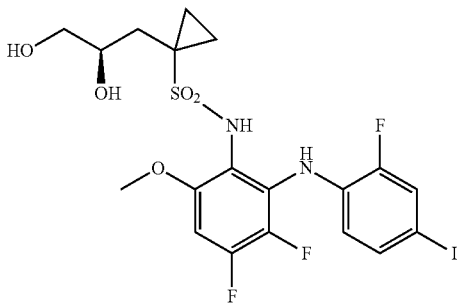

(R)-14

BACKGROUND TO THE INVENTION

N-{3,4-difluoro-2-[(2-fluoro-4-iodophenyl)amino]-6-methoxyphenyl}-1-[(2S)-2,3-dihydroxy-propyl]cyclopropanesulfonamide (hereinafter referred to as "(S)-14", "BAY 86-9766" or "RDEA 119") is a highly potent and selective MEK1/2 inhibitor currently under development in clinical trials for treatment of late stage cancer patients refractory or intolerant to other anticancer therapies [ref. 1].

The initial synthesis of (S)-14, shown in Scheme A, infra, published in US 2008/0058340 [ref. 2] comprises an osmium catalyzed dihydroxylation of the allyl sulfonamide substituted core followed by chromatographic separation of the enantiomers using a chiral stationary phase: the initial synthesis of (S)-14 provides the target compound as a racemic mixture that needs to be separated by chiral chromatography [ref. 2].

Scheme A: Racemic synthesis of (S)-14 according to US 2008/0058340:

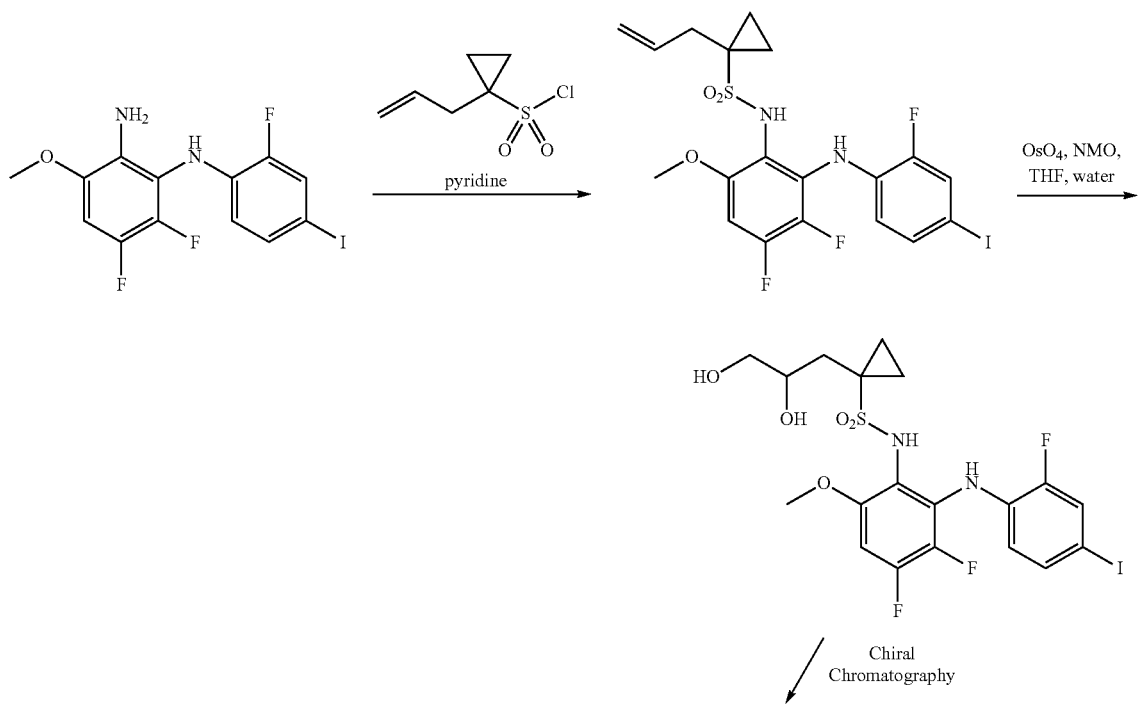

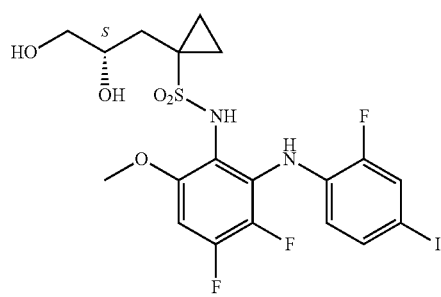 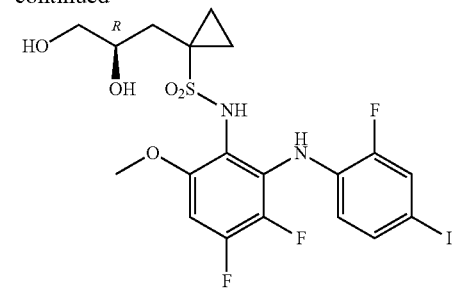

REDEA 119 ((S)-14)

NMO: 4-methylmorpholine 4-oxide monohydrate

In Scheme A, supra, a racemic mixture of the (S)- and (R)-enantiomers of N-{3,4-difluoro-2-[(2-fluoro-4-iodophenyl)amino]-6-methoxyphenyl}-1-[2,3-dihydroxy-propyl]cyclopropanesulfonamide is produced which, as seen, must be separated by chiral chromatography, in order to provide the single enantiomers. This separation of the enantiomers by chiral chromatography after the last step of the synthesis is a significant drawback in that in addition to the chiral separation step, more than double amounts of all intermediates have to be produced to obtain the same quantity of (S)-14 (RDEA 119).

As mentioned supra, another drawback of prior art synthesis of Scheme A is the use of very toxic osmium tetroxide which requires additional effort to remove the content of osmium to acceptable levels.

Another synthesis of (S)-14, shown in Scheme B, infra, published in PCT patent application under WO 2011/009541 A1 [ref. 7], describes a chiral preparation of (R)— and (S)— N-{3,4-difluoro-2-[(2-fluoro-4-iodophenyl)amino]-6-methoxyphenyl}-1-[2,3-dihydroxy-propyl]cyclopropanesulfonamide and protected derivatives thereof.

Scheme B, infra, illustrates the synthesis of (R)—N-(3,4-difluoro-2-(2-fluoro-4-iodophenylamino)-6-methoxyphenyl)-1-(2,3-dihydroxypropyl)cyclopropane-1-sulfonamide according to WO 2011/009541 A1 [ref. 7]:

SCHEME B

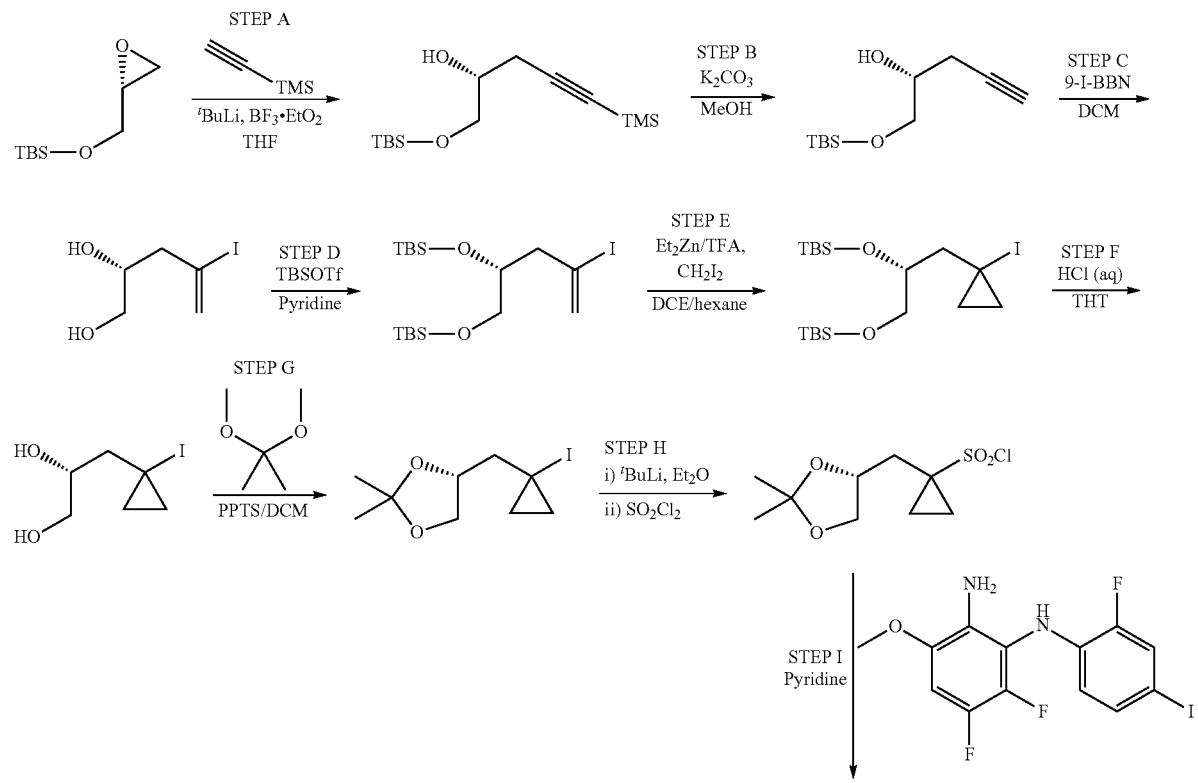

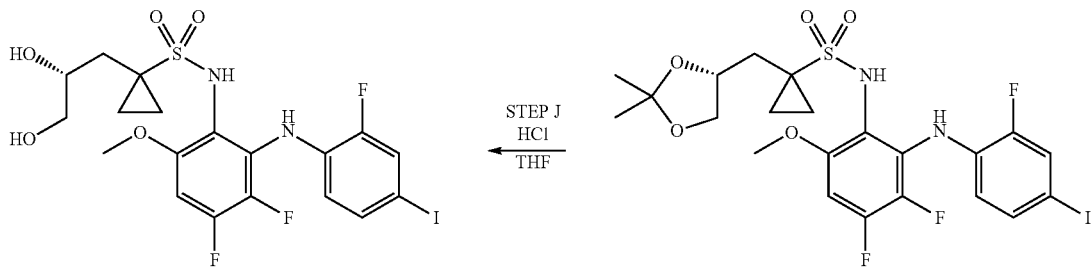

The synthesis as described in WO 2011/009541 A1 starts from commercially available glycidol which is converted via protection of the alcohol and coupling (Step A) with a protected acetylene followed by deprotection (Step B) and iodination with 9-I-BBN (Step C) to provide 4-iodopent-4-ene-1,2-diol, both HO groups of which are protected (Step D). A cyclopropyl group is introduced across the alkene of diol-protected 4-iodopent-4-ene-1,2-diol (Step E) to form the protected 3-(1-iodocyclopropyl)propane-1,2-diol derivative, which is then deprotected (Step F) and protected again (Step G), before the iodo group of which is transformed into a sulfonyl chloride group in Step H.

It has been discovered, and this provides the basis of the present invention, that (S)-14 can be synthesised via a chiral synthesis of sodium 1-{[(4S)-2,2-dimethyl-1,3-dioxolan-4-yl]methyl}cyclopropanesulfonate (hereinafter referred to also as compound "(S)-7") starting from (S)-epichlorohydrin (hereinafter is also referenced as compound "(S)-1") and alternatively from enantiomerically pure glycidol derivatives, as illustrated in Schemes 1 and 2, infra.

The R-enantiomers have been prepared in the same manner.

Scheme 1, infra, represents a general illustration of the steps used in the chiral synthesis of sodium 1-{[(4S)-2,2-dimethyl-1,3-dioxolan-4-yl]methyl}cyclopropanesulfonate ((S)-7) according to the present invention:

SCHEME 1

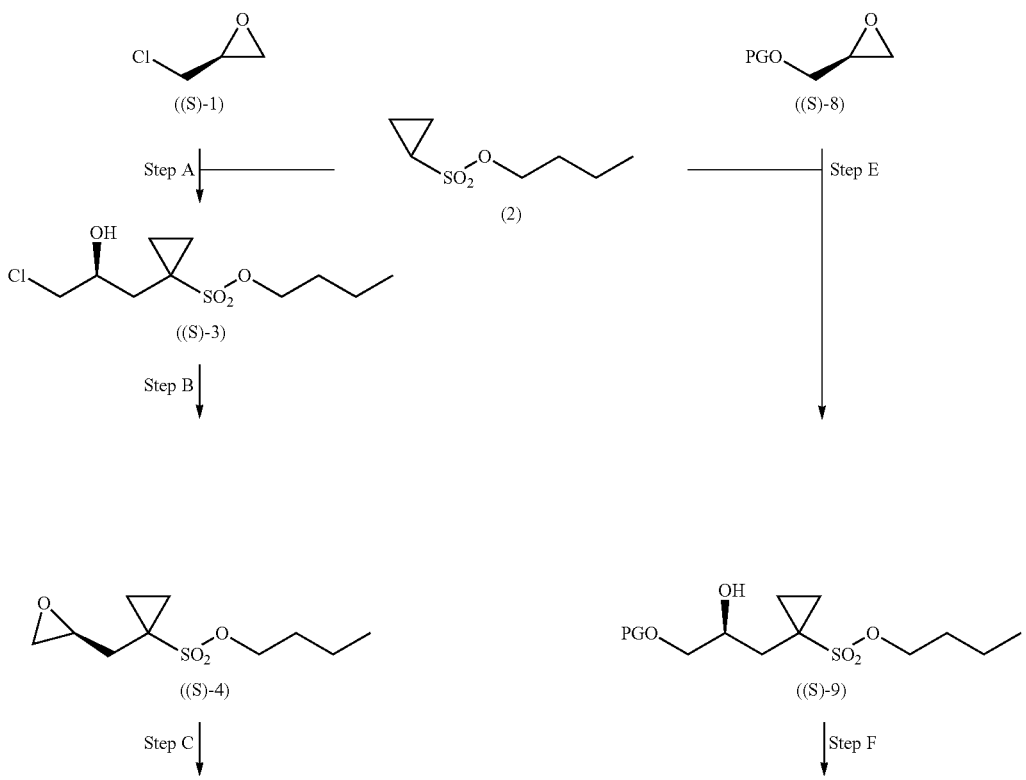

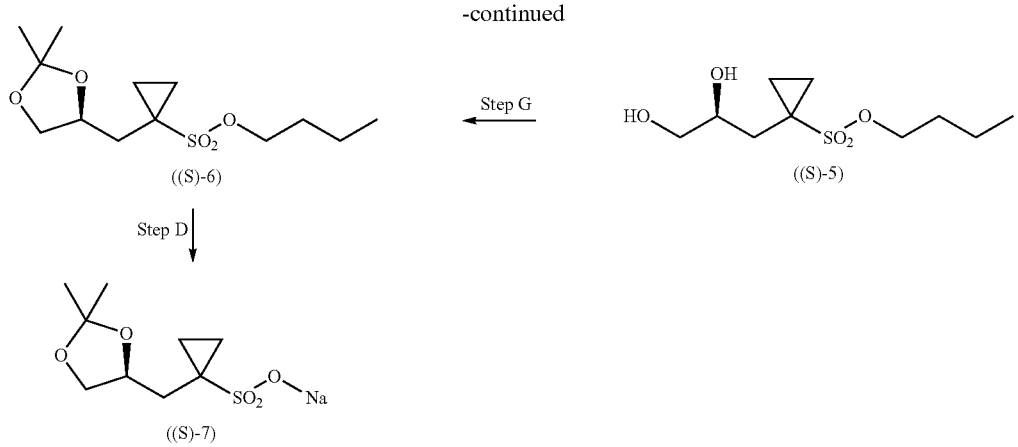

It is seen that the steps in Scheme 1 relate to the enantioselective synthesis of (S)-7, using the (S)-enantiomers of all the intermediates involved in said synthesis: as is understood by the person skilled in the art, the enantioselective synthesis of (R)-7 is identical to the synthesis of (S)-7 as illustrated in Scheme 1, supra, except that it uses the (R)-enantiomers of all the intermediates instead of the (S)-enantiomers.

Starting from economically priced chiral epoxypropane derivatives, chiral sodium 1-{[(4S)-2,2-dimethyl-1,3-dioxolan-4-yl]methyl}cyclopropanesulfonate ((S)-7) was prepared (Scheme 1, supra), which was converted to chiral 1-{[(4S)-2,2-dimethyl-1,3-dioxolan-4-yl]methyl}cyclopropane sulfonyl chloride (S)-10, which, in turn, was converted to the final product, N-{3,4-difluoro-2-[(2-fluoro-4-iodophenyl)amino]-6-methoxyphenyl}-1-[(2S)-2,3-dihydroxy-propyl]cyclopropanesulfonamide (S)-14), according to Scheme 2, infra.

Scheme 2, infra, represents a general illustration of the steps used in the chiral synthesis of N-{3,4-difluoro-2-[(2-fluoro-4-iodophenyl)amino]-6-methoxyphenyl}-1-[(2S)-2,3-dihydroxy-propyl]cyclopropanesulfonamide ((S)-14) from sodium 1-{[(4S)-2,2-dimethyl-1,3-dioxolan-4-yl]methyl}cyclopropanesulfonate ((S)-7) according to the present invention:

SCHEME 2

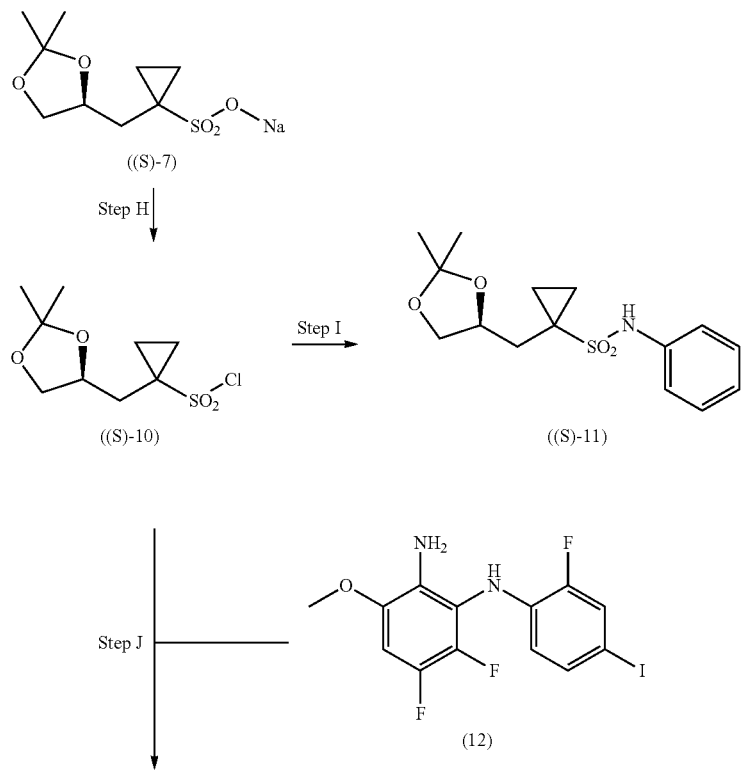

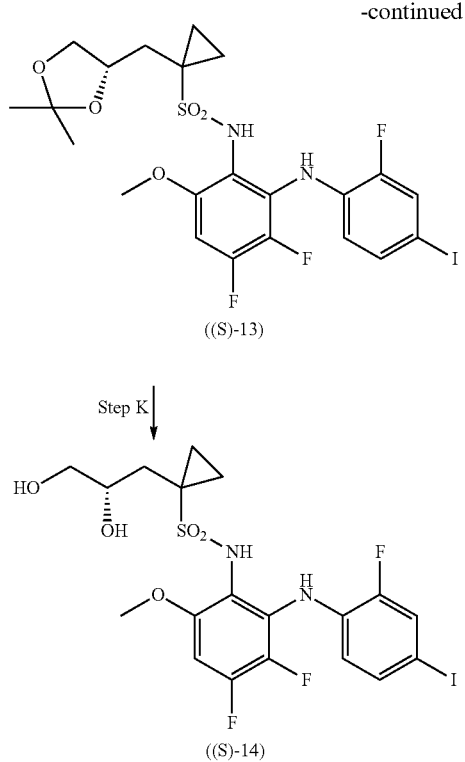

((S)-13)

Step K ((S)-14)

It is seen that the steps in Scheme 2 relate to the enantioselective synthesis of (S)-14, using the (S)-enantiomers of all the intermediates involved in said synthesis: as is understood by the person skilled in the art, the enantioselective synthesis of (R)-14 is identical to the synthesis of (S)-14, except that it uses the (R)-enantiomers of all the intermediates instead of the (S)-enantiomers.

The synthesis of RDEA 119 as depicted in Schemes 1 and 2 of the present invention delivers compound 14 containing 79-85% of the desired enantiomer (S)-14 (via steps A, B, C), hence, only 15-21% of the undesired isomer needs removing via chromatography. The amounts of intermediates and waste as well as the production costs of (S)-14 are thus reduced significantly using the synthesis of the present invention. Further, the use of toxic osmium tetroxide is avoided.

Further, the synthesis of RDEA 119 as depicted in Schemes 1 and 2 of the present invention delivers compound 14 as the desired enantiomer (S)-14 (via steps E, F, G), alleviating the technical problems of the separation of the enantiomers by chiral chromatography, and of the use of toxic osmium tetroxide. The amounts of intermediates and waste as well as the production costs of (S)-14 are thus reduced significantly using the synthesis of the present invention.

The synthesis of the sulfonyl chloride (S-10) depicted in Schemes 1 and 2 according to the present invention involves 5 steps (Steps A, B, C, D and H, or Steps E, F, G, D and H), including one protection step (Step C, starting from (S)-1, or Step G, starting from (S)-8).

Further, the synthesis of the sulfonyl chloride (S-10) depicted in Schemes 1 and 2 according to the present invention proceeds with an overall yield of >60% from (S)-8 (Steps, E, F, G, D, H).

All reagents used in the synthesis of the sulfonyl chloride (S-10) depicted in Schemes 1 and 2 according to the present invention (phosphoryl chloride, dimethoxypropane, sodium methoxide) are cheap and available in bulk.

The synthesis of the sulfonyl chloride (S-10) depicted in Schemes 1 and 2 according to the present invention provides the chiral sodium 1-{[(4S)-2,2-dimethyl-1,3-dioxolan-4-yl]methyl}cyclopropanesulfonate (S)-7, as an intermediate, which is a solid which can be purified by crystallization.

As seen in the Experimental section, Example 9b, it was found that the reaction of 1-{[(4R)-2,2-dimethyl-1,3-dioxolan-4-yl]methyl}cyclopropanesulfonyl chloride (compound (R)-10) with 5,6-difluoro-N1-(4-fluoro-2-iodophenyl)-3-methoxybenzene-1,2-diamine (compound 12), in the presence of 4-dimethylaminopyridine in pyridine, provided, under the conditions described, only a percentage yield of 38.9% of N-{3,4-difluoro-2-[(2-fluoro-4-iodophenyl)amino]-6-methoxyphenyl}-1-{[(4R)-2,2-dimethyl-1,3-dioxolan-4-yl]methyl}cyclopropanesulfonamide (compound (R)-13). However, surprisingly, the bromide-promoted method of the present invention as depicted in Scheme 2, Steps J and K) provides the pure (S)-14 product in very good yield: as seen specifically in the Experimental section, Example 9a, it was surprisingly found that the reaction of 1-{[(4S)-2,2-dimethyl-1,3-dioxolan-4-yl]methyl}cyclopropanesulfonyl chloride (compound (S)-10) with 5,6-difluoro-N1-(4-fluoro-2-iodophenyl)-3-methoxybenzene-1,2-diamine (compound 12), in the presence of tetrabutylammonium bromide in pyridine and sulfolane, provided, under the conditions described, a percentage yield of 92.2% of N-{3,4-difluoro-2-[(2-fluoro-4-iodophenyl)amino]-6-methoxyphenyl}-1-{[(4S)-2,2-dimethyl-1,3-dioxolan-4-yl]methyl}cyclopropanesulfonamide (compound (S)-13), thus representing an increase in percentage yield of product of over 50% when directly comparing the method in Example 9a with the method in Example 9b. This is clearly advantageous from a chemical developmental point of view, in view of the productivity of the method and the decrease in the amount of impurities.

Further, more importantly, as seen in the Experimental Section, Example 10a, it was surprisingly found that:

the reaction of 1-{[(4S)-2,2-dimethyl-1,3-dioxolan-4-yl]methyl}cyclopropanesulfonyl chloride (compound (S)-10) with 5,6-difluoro-N1-(4-fluoro-2-iodophenyl)-3-methoxybenzene-1,2-diamine (compound 12), in the presence of tetrabutylammonium bromide in pyridine and sulfolane, then, after complete conversion to N-{3,4-difluoro-2-[(2-fluoro-4-iodophenyl)amino]-6-methoxyphenyl}-1-{[(4S)-2,2-dimethyl-1,3-dioxolan-4-yl]methyl}cyclopropanesulfonamide (compound (S)-13), followed by stirring the resulting reaction mixture with hydrochloric acid, provided, under the conditions described, a percentage yield of 91.6% of N-{3,4-difluoro-2-[(2-fluoro-4-iodophenyl)amino]-6-methoxyphenyl}-1-[(2S)-2,3-dihydroxy-propyl]cyclopropanesulfonamide (compound (S)-14): this "one-pot" method of Example 10a is clearly advantageous from a chemical developmental point of view, in terms of process efficiency.

Further, it was surprisingly found that the preparation of (S)-13 from (S)-10-Br and the one pot conversion to R-14 proceeds much cleaner and at a temperature of 23° C., as compared to the preparation of (S)-13 from (S)-10 and the one pot conversion to R-14, which proceeds at a temperature of 70° C.

The method of preparation of (S)-14 from (S)-10 of the present invention, particularly the one-pot method of preparing (S)-14 from (S)-10, as described and defined herein, is thus clearly surprisingly technically advantageous.

The following description provides further general details of each step shown in Schemes 1 and 2, supra, together with the technical advantages thereof.

I. In Re. Scheme 1, Steps a, B, C, E, F, G, and D, Supra

Synthesis of Butyl 1-{[(4S)-2,2-dimethyl-1,3-dioxolan-4-yl]methyl}cyclo propanesulfonates 6

Deprotonation of butyl cyclopropanesulfonate 2 with n-butyllithium and reaction with (S)-epichlorohydrin (S)-1 provided the chloroalcohol 3 in good yield (vide Scheme 1, Step A, supra, and Scheme 3, infra). Chloroalcohol 3 was converted quantitatively to the epoxide 4 with aqueous sodium hydroxide in tetrahydrofuran (vide Scheme 1, Step B, and Scheme 3, infra).

Scheme 3: Stereoselective synthesis of epoxides 4 starting from (S)-epichlorohydrin (S)-1:

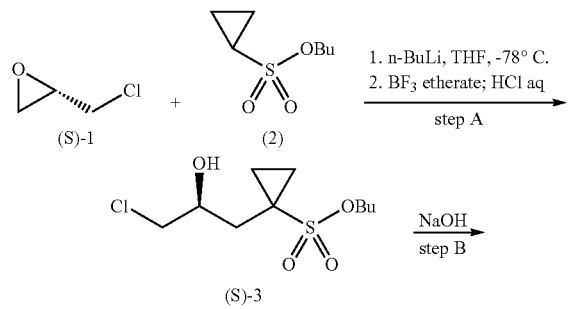

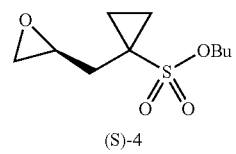

Performing the first step of the sequence without additives resulted in up to 65% by-product formation caused by competitive self alkylation (vide Scheme 4, infra). Several additives such as TMEDA (N,N,N',N'-Tetramethylethylenediamine), DMI (1,3-Dimethyl-2-imidazolidinone), DMPU (1,3-Dimethyl-3,4,5,6-tetrahydro-2(1H)-pyrimidinone), CuI, LiI were screened but showed no significant improvement: it was surprisingly found that 1 equivalent of boron trifluoride etherate led to a significant decrease in by-product formation:

Scheme 4: By-product formation

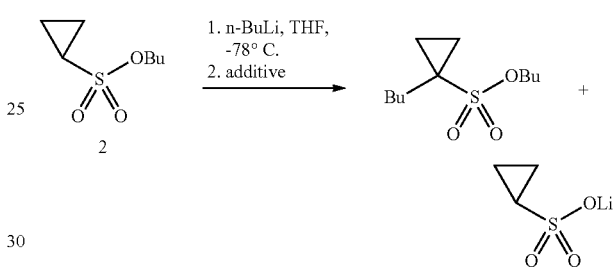

From reactions performed with magnesium bromide, 1-bromo-3-chloropropan-2-ol was isolated as the only product, no conversion was observed when triethylborane was used as additive.

Of all additives tested, boron trifluoride etherate was identified as the most promising. Good results have been obtained with 1.0 equivalent of boron trifluoride etherate whereas more equivalents resulted in formation of polymers.

The reaction of isopropyl cyclopropanesulfonate with (S)-2-(benzyloxymethyl)oxirane in the presence of 0.83 equivalents of hexamethyl phosphoric triamide (HMPT) was published in international patent application WO 2010/145197 A1 [ref. 3]. As HMPT exhibits carcinogenic and mutagenic properties, it was preferred to use boron trifluoride etherate instead of HMPT as additive for industrial preparation (vide Scheme 5, infra).

Scheme 5: Direct conversion of epoxides 4 to dioxolanes 6 (vide Scheme 1, Step C, supra):

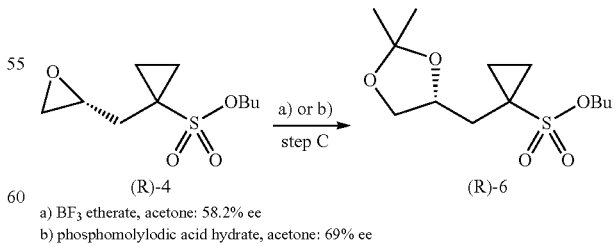

a) BF$_3$ etherate, acetone: 58.2% ee
b) phosphomolylodic acid hydrate, acetone: 69% ee As shown with (R)-4 direct conversion of the epoxide 4 with acetone catalyzed by boron trifluoride etherate or phosphomolybdic acid hydrate yielded dioxolane 6 as a mixture of enantiomers with 58.2 and 69.8% ee respectively (scheme 5).

Alternatively, chiral diol 5 was obtained, without racemization, from TBDMS- and THP-protected glycidols (9a and 9b, respectively) and butyl cyclopropanesulfonate (2) under the same conditions optimized for the preparation of chloroalcohol 3 in good yield (vide Scheme 1, Step E, supra). Fortunately, TBDMS- and THP-protecting groups could be easily removed by acidic treatment of protected intermediates 9a and 9b providing enantiomerically pure dial 5 (vide Scheme 1, Step F, supra, and Scheme 6, infra).

mutagenic properties we preferred boron trifluoride etherate to HMPT as additive for industrial preparation.

Chiral diol 5 was obtained without racemization from TBDMS- as well as THP-protected glycidols (8a and 8b, respectively) and butyl cyclopropanesulfonate 2.

Fortunately TBDMS- and THP-protecting groups could be easily removed by acidic treatment providing enantiomerically pure dial 5 (vide scheme 1, step F, supra).

Scheme 6: Chiral synthesis starting from protected glycidols

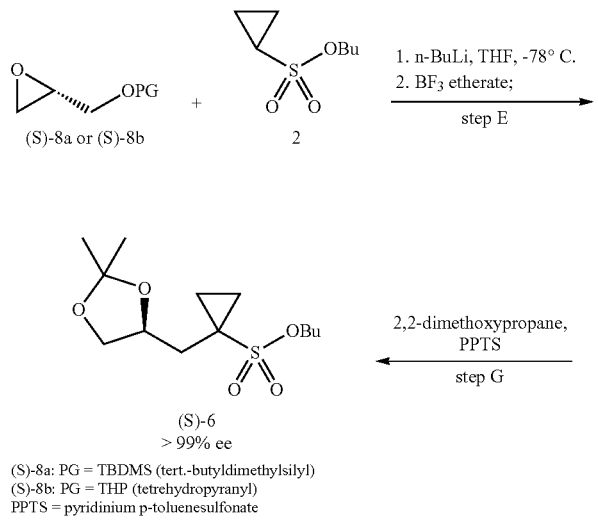
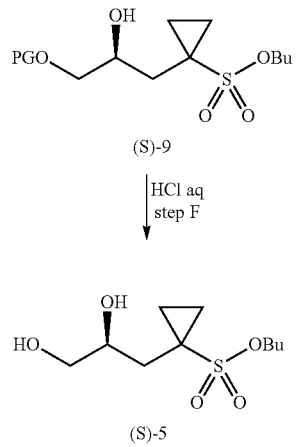

(S)-8a: PG = TBDMS (tert.-butyldimethylsilyl)
(S)-8b: PG = THP (tetrehydropyranyl)
PPTS = pyridinium p-toluenesulfonate Reactions performed without additives resulted in up to 65% by-product formation caused by competitive self alkylation (vide Scheme 7, infra). Therefore several additives like TMEDA, DMI, DMPU, CuI, LiI were screened but showed no significant improvement (vide Scheme 7, infra).

Chiral diol 5 was converted subsequently to the desired dioxolane 6 with 2,2-dimethoxypropane catalyzed by pyridinium p-toluenesulfonate in good yield (vide Scheme 1, Step G, supra).

Scheme 7: By-product formation

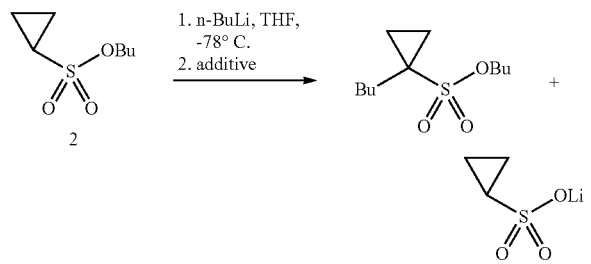

From reactions performed with magnesium bromide 1-bromo-3-chloro-propan-2-ol was isolated as sole product, no conversion was observed when triethylborane was used as additive. Of all additives tested boron trifluoride etherate was identified as most promising. Good results have been obtained with 1.0 equivalent of boron trifluoride etherate whereas more equivalents resulted in formation of polymers.

The reaction of isopropyl cyclopropanesulfonate with (S)-2-(benzyloxymethyl)oxirane in the presence of 0.83 equivalents of hexamethyl phosphoric triamide (HMPT) was published [ref. 3]. As HMPT exhibits carcinogenic and II. In Re. Scheme 2, Steps H, J (and I), and K, Supra Synthesis of (S)-14 via sulfonyl chloride (S)-10

As seen supra, formation of sodium sulfonate 7 was achieved by using sodium methoxide instead of the considerably more expensive potassium thiocyanate [refs. 1,2] (vide Scheme 1, Step D, supra, and Scheme 8, infra). Pure sodium sulfonate 7 was obtained from crystallization with ethanol or isopropanol. Reaction of 7 in pyridine with phosphoryl chloride [ref. 4] proved to be a more economical route to sulfonyl chloride 10 compared to cyanuric chloride [ref. 5] as chlorination reagent (vide Scheme 2, Step H, supra, and Scheme 8, infra). After aqueous work up, 10 was obtained in good yield without deterioration of the dioxolane protecting group. Reactions with oxalyl chloride or triphenylphosphine/sulfurylchloride [ref. 6] were less effective. Enantiomeric purity of 10 was assessed by chiral HPLC of the corresponding anilides 11 (vide Scheme 2, Step I, supra, and Scheme 8, infra). The reaction of sulfonyl chloride 10 with aniline was accelerated by addition of lithium bromide.

Scheme 8: Synthesis of chiral amides

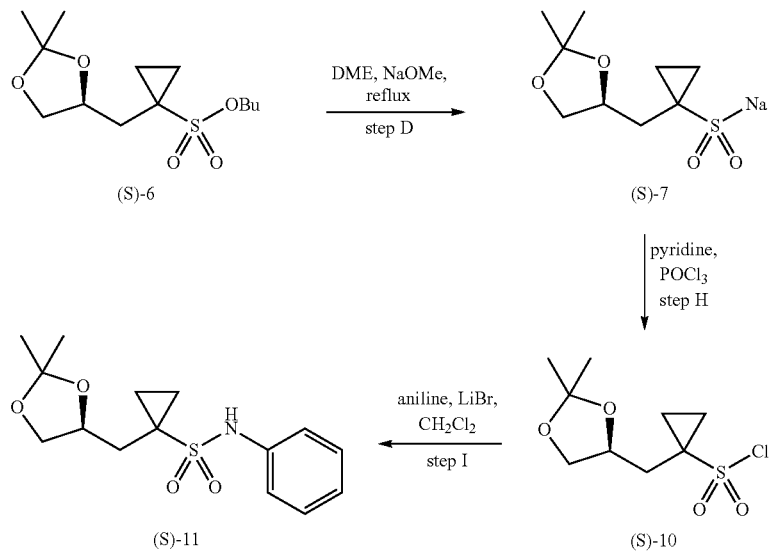

Starting from sulfonyl chloride (S)-10 enantiomerically pure (S)-14 was prepared with tetrabutyl ammonium bromide as additive at 70° C. in sulfolane/pyridine 2:1 followed by acidic deprotection of (S)-13 during aqueous work up (vide Scheme 2, Step K, supra, and Scheme 9, infra). The amide formation was accelerated by addition of tetrabutyl ammonium bromide (vide Scheme 9, infra).

Sulfonyl chloride (R)-10 furnished the enantiomer (R)-14 accordingly (vide Scheme 9, infra).

The enantiomeric purity of 14 was determined by chiral HPLC.

Scheme 9: Stereoselective synthesis of (S)-14

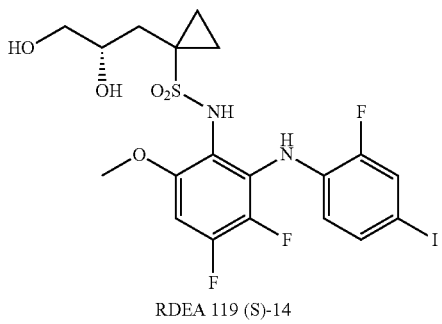

-continued

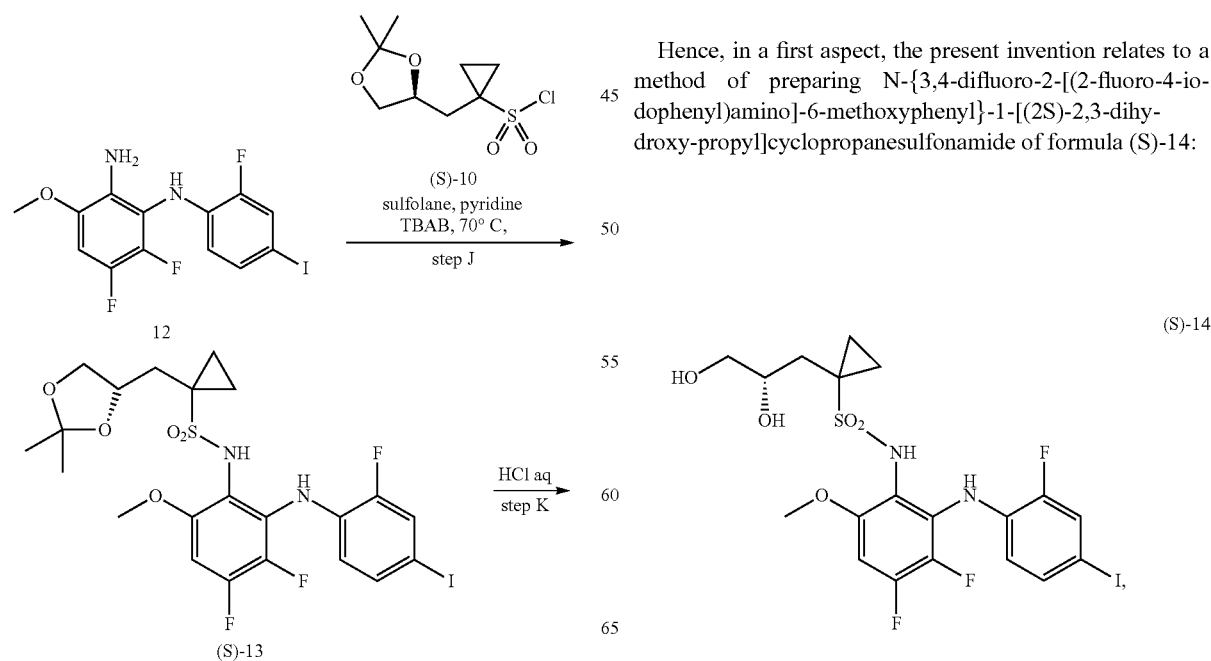

RDEA 119 (S)-14

Hence, in a first aspect, the present invention relates to a method of preparing N-{3,4-difluoro-2-[(2-fluoro-4-iodophenyl)amino]-6-methoxyphenyl}-1-[(2S)-2,3-dihydroxy-propyl]cyclopropanesulfonamide of formula (S)-14:

via the following steps shown in Schemes 1 and 2, infra:
SCHEME 1
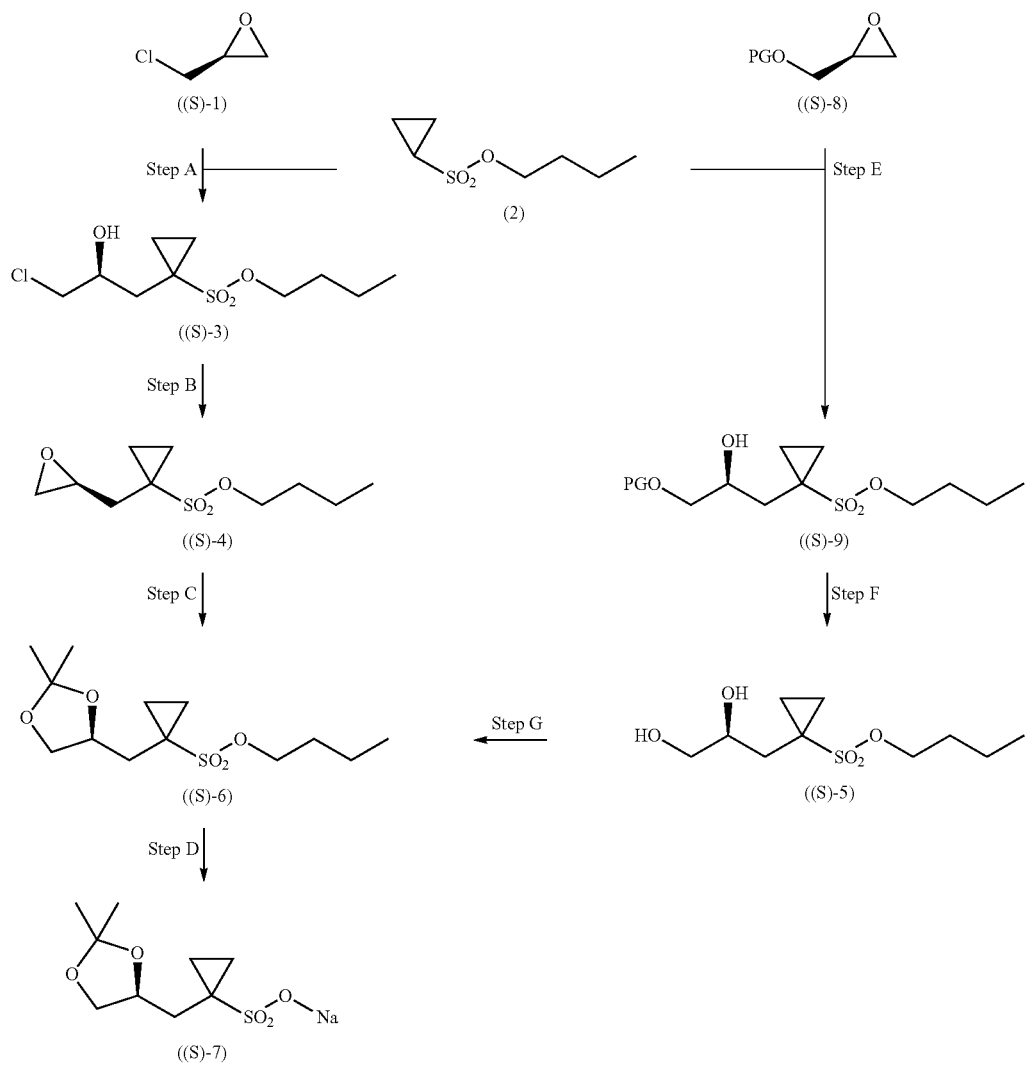
SCHEME 2
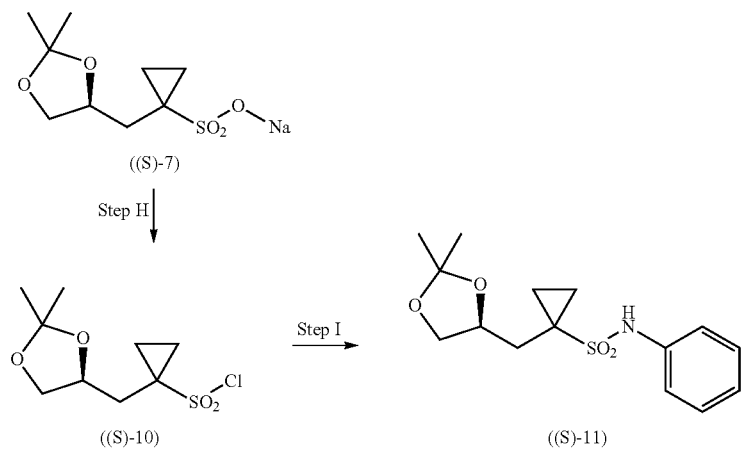

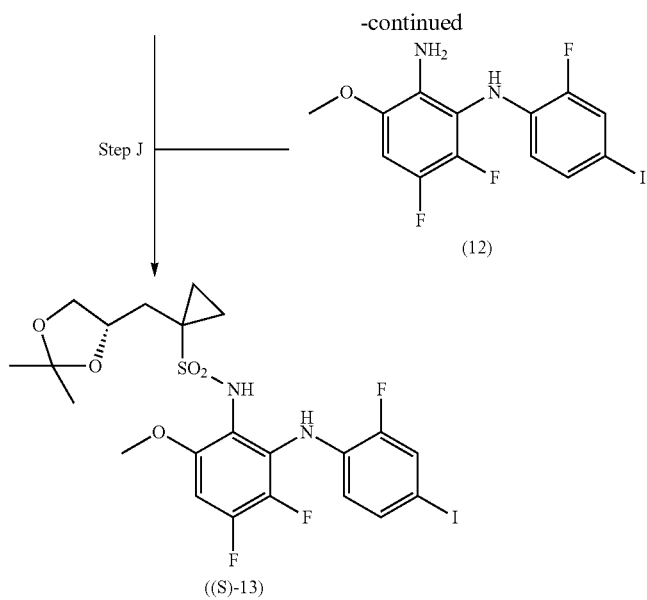
In an embodiment of the first aspect, the present invention relates to a method of preparing a compound of formula (S)-14:
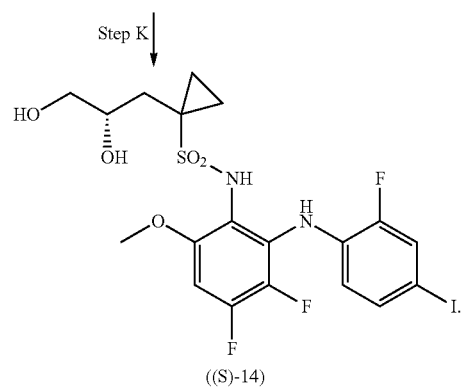
(S)-14
comprising:
i) the following step J:
wherein a compound of formula (S)-10:
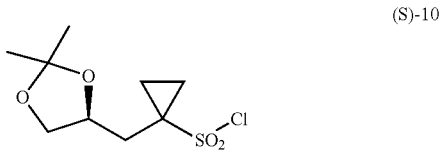
(S)-10
is allowed to react with a compound of formula (12):
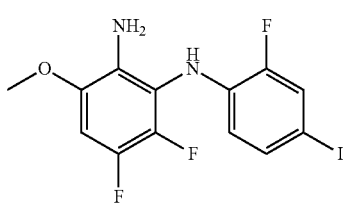
(12)

in the presence of a bromide, such as tetra-n-butylammonium bromide or lithium bromide for example, optionally in the presence of a base, such as pyridine for example, optionally in a solvent, such as sulfolane for example,
thereby providing a reaction mixture containing a compound of formula (S)-13:

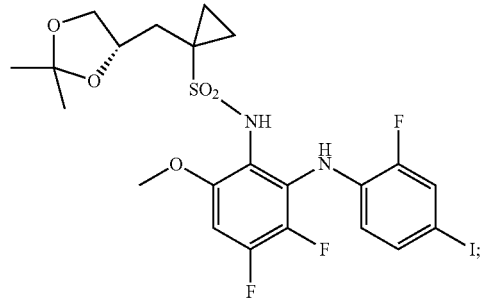

((S)-13)

and, then, ii) the following step K:

wherein an aqueous mineral acid, such as hydrochloric acid for example, is added to said reaction mixture containing a compound of formula (S)-13, thereby providing a compound of formula (S)-14.

Alternatively, in the above-mentioned step J, a catalyst, such as 4-dimethylaminopyridine for example, can be used instead of said bromide.

Alternatively, in scheme 2, step J, the compound of formula (S)-10-Br:

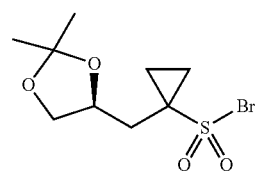

(S)-10-Br may be used instead of the compound (S)-10.

Hence, in an embodiment of the first aspect, the present invention relates to a method of preparing a compound of formula (S)-14:

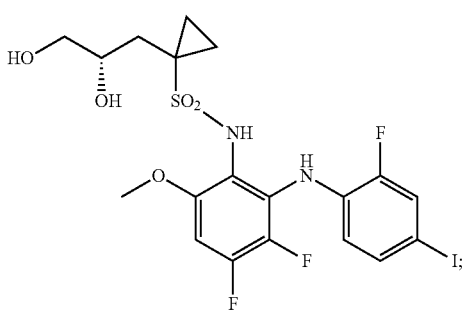

(S)-14 comprising:

i) the following step J:

wherein a compound of formula (S)-10-Br:

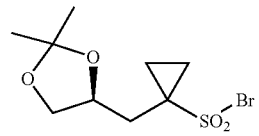

(S)-10-Br is allowed to react with a compound of formula (12):

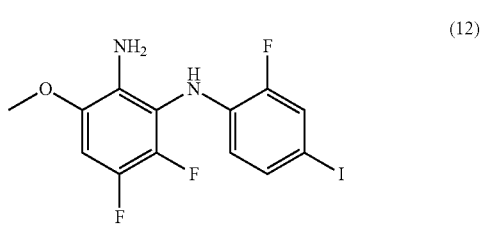 [SMILES: COc1cc(F)c(F)c(Nc2ccc(I)cc2F)c1N]

(12)

optionally in the presence of a base, such as pyridine for example, optionally in a solvent, such as sulfolane for example, thereby providing a reaction mixture containing a compound of formula (S)-13:

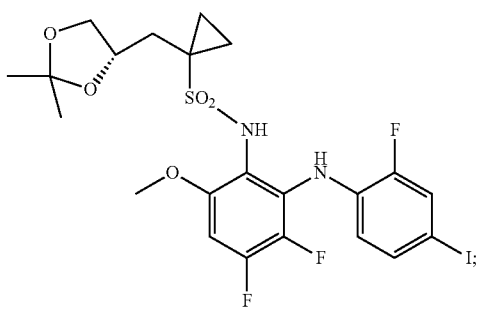

((S)-13)

and, then, ii) the following step K:

wherein an aqueous mineral acid, such as hydrochloric acid for example, is added to said reaction mixture containing a compound of formula (S)-13, thereby providing a compound of formula (S)-14.

In another embodiment of the first aspect, the present invention relates to a method of preparing a compound of formula (S)-14:

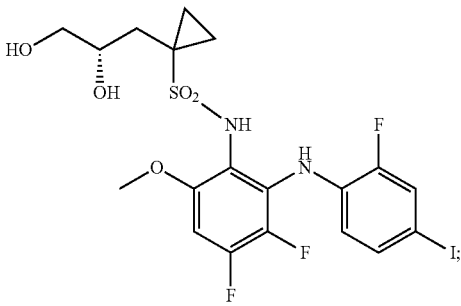

(S)-14 comprising the following step K:
wherein an aqueous mineral acid, such as hydrochloric acid for example, is added to a compound of formula (S)-13:

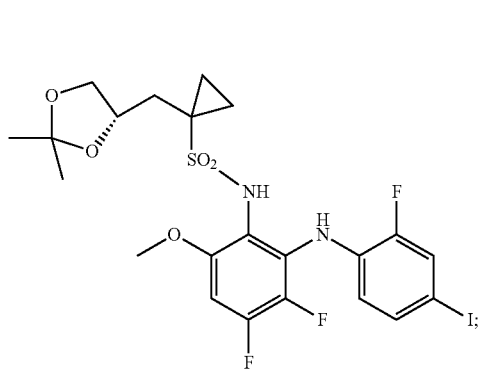

((S)-13)

thereby providing a compound of formula (S)-14.

In a further embodiment of the first aspect of the present invention, the above-mentioned compound of formula (S)-13:

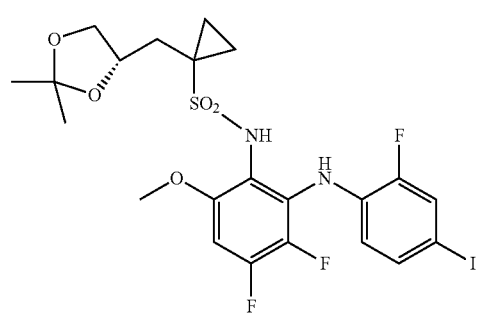

((S)-13)

is prepared by the following step J:
wherein a compound of formula (S)-10:

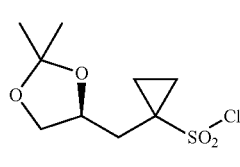

(S)-10 is allowed to react with a compound of formula (12):

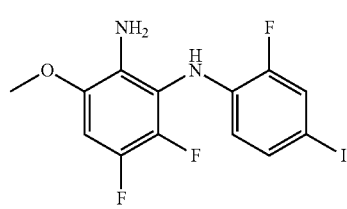

(12)

in the presence of a bromide, such as tetra-n-butylammonium bromide or lithium bromide for example, optionally in the presence of a base, such as pyridine for example, optionally in a solvent, such as sulfolane for example, thereby providing a reaction mixture containing a compound of formula (S)-13:

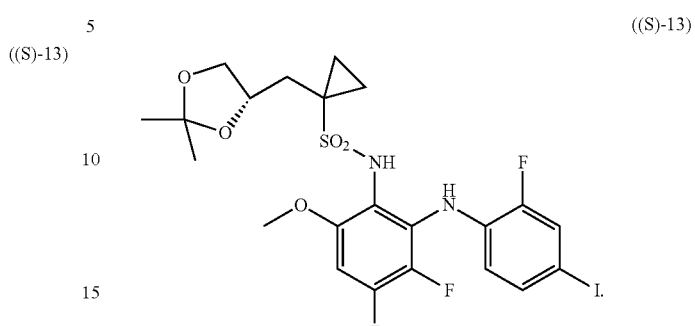

((S)-13)

Alternatively, in the above-mentioned step J, a catalyst, such as 4-dimethylaminopyridine for example, can be used instead of said bromide.

In a further embodiment of the first aspect of the present invention, the above-mentioned compound of formula (S)-13:

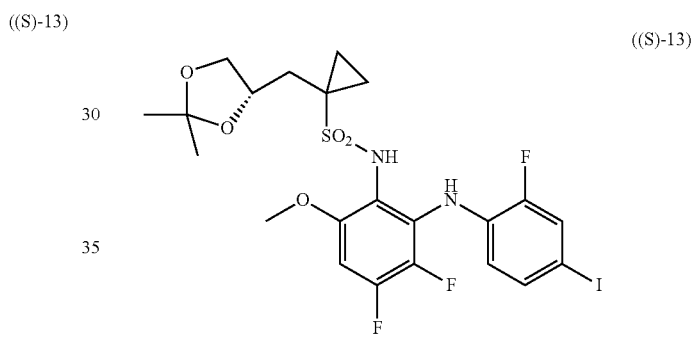

((S)-13)

is prepared by the following step J:
wherein a compound of formula (S)-10-Br:

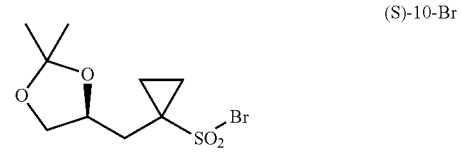

(S)-10-Br is allowed to react with a compound of formula (12):

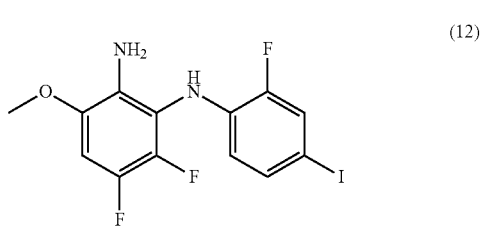 [SMILES: COc1cc(F)c(F)c(Nc2ccc(I)cc2F)c1N]

(12)

optionally in the presence of a base, such as pyridine for example, optionally in a solvent, such as sulfolane for example, thereby providing a reaction mixture containing a compound of formula (S)-13:

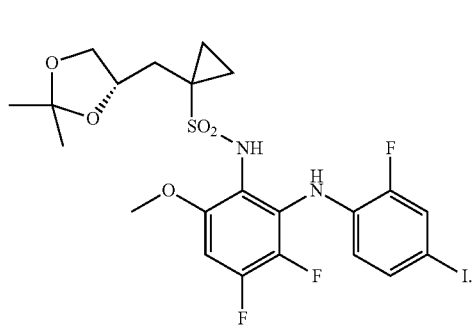
((S)-13)

In a further embodiment of the first aspect of the present invention, the above-mentioned compound of formula (S)-10:

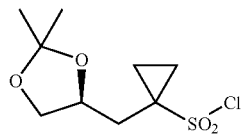
(S)-10 is prepared by allowing a compound of formula (S)-7:

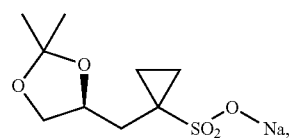
(S)-7 to react with a chlorinating agent, such as P(O)Cl$_3$, PCl$_3$ or SOCl$_2$ for example, optionally in a solvent, such as pyridine for example, thereby providing a compound of formula (S)-10.

In a further embodiment of the first aspect of the present invention, the above-mentioned compound of formula (S)-10-Br:

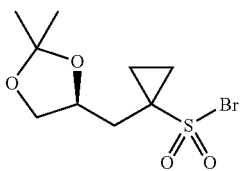
(S)-10-Br is prepared by allowing a compound of formula (S)-7:

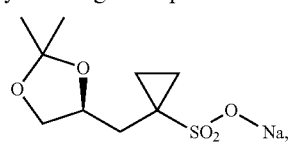
(S)-7 to react with a brominating agent, such as P(O)Br$_3$ or PBr$_3$ for example, optionally in a solvent, such as pyridine for example, thereby providing a compound of formula (S)-10-Br.

In a further embodiment of the first aspect of the present invention, the above-mentioned compound of formula (S)-7:

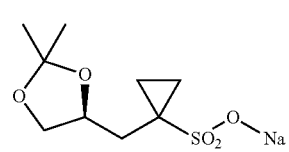
(S)-7 is prepared by allowing a compound of formula (S)-6:

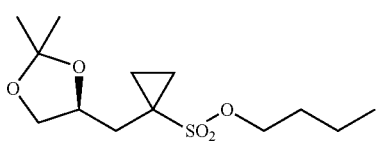
(S)-6 to react with a sodium alkoxide, such as sodium methoxide for example, optionally in a solvent, such as methanol for example, thereby providing a compound of formula (S)-7.

In a further embodiment of the first aspect, the present invention relates to a method of preparing a compound of formula (S)-10:

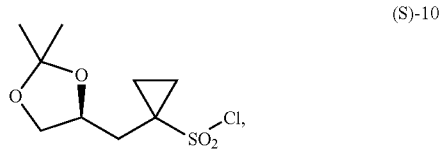
(S)-10 wherein a compound of formula (S)-7':

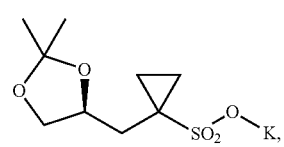
(S)-7' is allowed to react with a chlorinating agent, such as P(O)Cl$_3$, PCl$_3$ or SOCl$_2$ for example, optionally in a solvent, such as pyridine for example, thereby providing a compound of formula (S)-10.

In a further embodiment of the first aspect of the present invention, the above-mentioned compound of formula (S)-7':

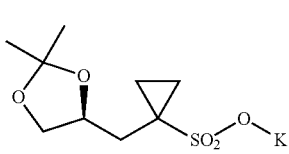
(S)-7' is prepared by allowing a compound of formula (S)-6:

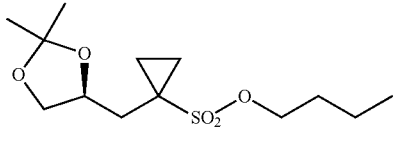
(S)-6 to react with a potassium alkoxide, such as potassium methoxide for example, optionally in a solvent, such as methanol for example, thereby providing a compound of formula (S)-7'.

A further embodiment of the first aspect of the present invention relates to a method of preparing N-{3,4-difluoro-2-[(2-fluoro-4-iodophenyl)amino]-6-methoxyphenyl}-1-[(2S)-2,3-dihydroxy-propyl]cyclopropanesulfonamide of formula (S)-14:

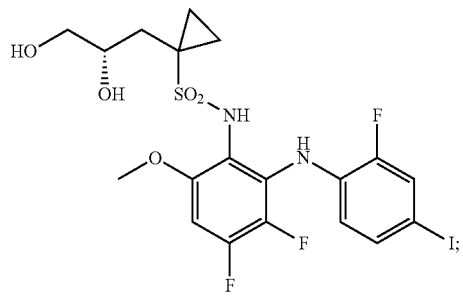
(S)-14 comprising the following step D:
wherein a compound of formula (S)-6:

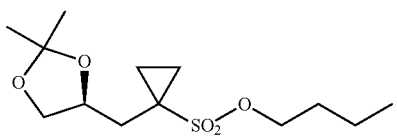
(S)-6 is allowed to react with a sodium alkoxide, such as sodium methoxide for example, optionally in a solvent, such as methanol for example, thereby providing a compound of formula (S)-7:

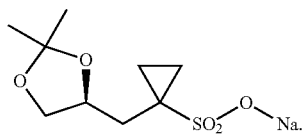
(S)-7

A further embodiment of the first aspect of the present invention relates to a method of preparing N-{3,4-difluoro-2-[(2-fluoro-4-iodophenyl)amino]-6-methoxyphenyl}-1-[(2S)-2,3-dihydroxy-propyl]cyclopropanesulfonamide of formula (S)-14:

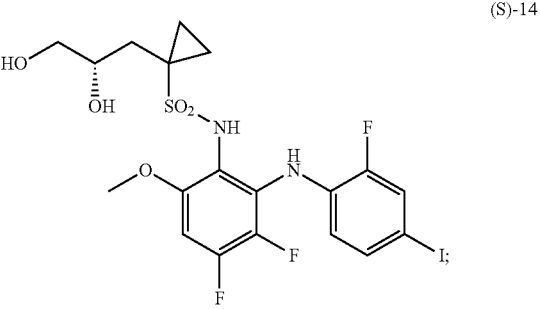 [SMILES: COc1cc(F)c(F)c(Nc2ccc(I)cc2F)c1NS(=O)(=O)C1(C[C@H](O)CO)CC1]
(S)-14 comprising the following step D:
wherein a compound of formula (S)-6:

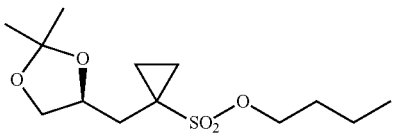
(S)-6 is allowed to react with a potassium alkoxide, such as potassium methoxide for example, optionally in a solvent, such as methanol for example, thereby providing a compound of formula (S)-7':

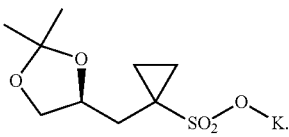
(S)-7'

In a further embodiment of the first aspect of the present invention, the above-mentioned compound of formula (S)-6:

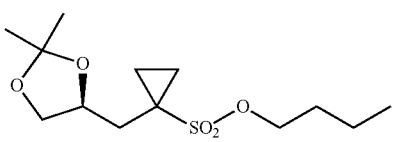
(S)-6 is prepared by allowing a compound of formula (S)-4:

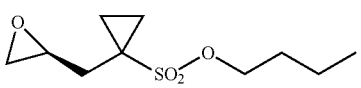
(S)-4 to react with either:
a) boron trifluoride, optionally in the form of a complex, such as a boron trifluoride etherate complex for example, such as a boron trifluoride tetrahydrofuran complex, or a boron trifluoride diethylether complex for example, optionally in a solvent such as acetone for example, or b) phosphomolybdic acid hydrate, optionally in a solvent such as acetone for example, thereby providing a compound of formula (S)-6.

In a further embodiment of the first aspect of the present invention, the above-mentioned compound of formula (S)-4:

(S)-4 is prepared by allowing a compound of formula (S)-3:

(S)-3 to react with a base, such as sodium hydroxide for example, optionally in a solvent, such as water for example, thereby providing a compound of formula (S)-4.

In a further embodiment of the first aspect of the present invention, the above-mentioned compound of formula (S)-3: is prepared by:

(S)-3 a) allowing a compound of formula 2:

(2)

to react with a base, such as n-butyllithium for example, optionally in a solvent, such as tetrahydrofuran for example, b) adding a compound of formula (S)-1 and boron trifluoride, optionally in the form of a complex, such as a boron trifluoride etherate complex for example, such as a boron trifluoride tetrahydrofuran complex, or a boron trifluoride diethylether complex for example; and c) allowing the thus-formed deprotonated compound of formula 2 to react with a compound of formula (S)-1:

(S)-1 thereby providing a compound of formula (S)-3.

In a further embodiment of the first aspect of the present invention, the above-mentioned compound of formula (S)-6:

(S)-6 is prepared by allowing a compound of formula (S)-5:

(S)-5 to react with 2,2-dimethoxypropane, optionally in a solvent, such as tetrahydrofuran for example and optionally in the presence of a catalyst, such as pyridinium p-toluenesulfonate for example, thereby providing a compound of formula (S)-6.

In a further embodiment of the first aspect of the present invention, the above-mentioned compound of formula (S)-5:

(S)-5 is prepared by allowing a compound of formula (S)-9:

(S)-9 wherein PG represents a protecting group, such as a t-butyldimethylsilyl- group (compound (S)-9a) or a tetrahydropyranyl group (compound (S)-9b), for example, to react with an acid, such as hydrochloric acid or p-toluene sulfonic acid for example, optionally in a solvent, such as methanol for example, thereby providing a compound of formula (S)-5.

In a further embodiment of the first aspect of the present invention, the above-mentioned compound of formula (S)-9:

(S)-9 wherein PG represents a t-butyldimethylsilyl- group (compound (S)-9a) or a tetrahydropyranyl group (compound (S)-9b), is prepared by:

a) allowing a compound of formula 2:

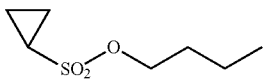

(2)

to react with a base, such as n-butyllithium for example, optionally in a solvent, such as tetrahydrofuran for example, b) adding a compound of formula (S)-8 and boron trifluoride, optionally in the form of a complex, such as a boron trifluoride etherate complex for example, such as a boron trifluoride tetrahydrofuran complex, or a boron trifluoride diethylether complex for example; and c) allowing the thus-formed deprotonated compound of formula 2 to react with a compound of formula (S)-8:

(S)-8 wherein PG represents a t-butyldimethylsilyl- group (compound (S)-8a) or a tetrahydropyranyl group (compound (S)-8b), respectively, thereby providing a compound of formula (S)-9.

In a further embodiment of the first aspect, the present invention relates to a method of preparing the compound of formula (S)-14, wherein each of said steps A to K as shown in Schemes 1 and 2, supra, are described in relation to Schemes 3 to 9, supra.

In accordance with a second aspect, the present invention relates to intermediate compounds which are useful in the preparation of the above-mentioned compound of formula (S)-14.

In an embodiment of said second aspect, the present invention relates to a compound:

1-{[(4S)-2,2-dimethyl-1,3-dioxolan-4-yl]methyl}cyclopropanesulfonyl bromide (S)-10-Br

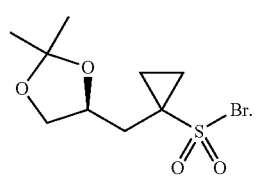

(S)-10-Br

In an embodiment of said second aspect, the present invention relates to a compound:

potassium 1-{[(4S)-2,2-dimethyl-1,3-dioxolan-4-yl]methyl}cyclopropane-sulfonate (S)-7'

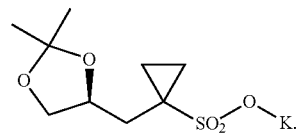

(S)-7'

In an embodiment of said second aspect, the present invention relates to a compound:

Butyl 1-{[(4S)-2,2-dimethyl-1,3-dioxolan-4-yl]methyl}cyclo propane sulfonate (S)-6

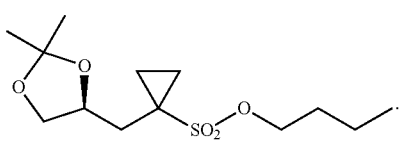

(S)-6

In an embodiment of said second aspect, the present invention relates to a compound:

Butyl 1-[(2S)-2,3-dihydroxypropyl]cyclopropanesulfonate (S)-5

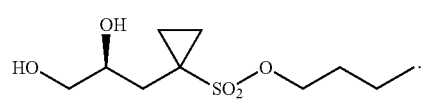

(S)-5

In an embodiment of said second aspect, the present invention relates to a compound:

Butyl 1-[(2S)-oxiran-2-ylmethyl]cyclopropanesulfonate (S)-4

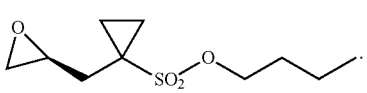

(S)-4

In an embodiment of said second aspect, the present invention relates to a compound:

Butyl 1-[(2S)-3-chloro-2-hydroxypropyl]cyclopropanesulfonate (S)-3

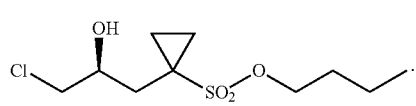

(S)-3

In an embodiment of said second aspect, the present invention relates to a compound:

Butyl 1-[(2S)-3-{[tert-butyl(dimethyl)silyl]oxy}-2-hydroxypropyl]cyclopropane-sulfonate (S)-9a

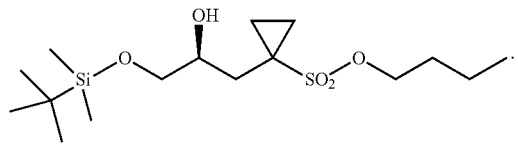

(S)-9a

In an embodiment of said second aspect, the present invention relates to a compound:

Butyl 1-[(2S)-2-hydroxy-3-(tetrahydro-2H-pyran-2-yloxy)propyl]cyclopropane sulfonate (S)-9b

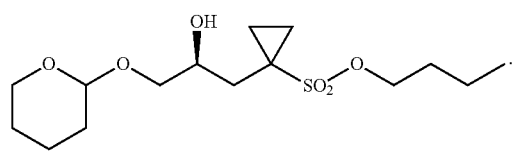

(S)-9b

In a third aspect, the present invention relates to the use of the intermediate compounds according to the second aspect, supra, for preparing the compound of formula (S)-14, supra.

In an embodiment of said third aspect, the present invention relates to the use of:

1-{[(4S)-2,2-dimethyl-1,3-dioxolan-4-yl]methyl}cyclopropanesulfonyl bromide (S)-10-Br

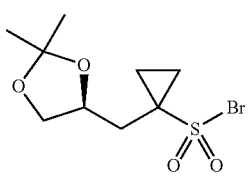

(S)-10-Br for preparing the compound of formula (S)-14, supra.

In an embodiment of said third aspect, the present invention relates to the use of:

potassium 1-{[(4S)-2,2-dimethyl-1,3-dioxolan-4-yl]methyl}cyclopropane-sulfonate (S)-7'

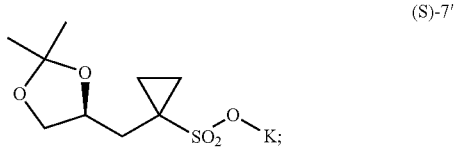

(S)-7' for preparing the compound of formula (S)-14, supra.

In an embodiment of said third aspect, the present invention relates to the use of:

Butyl 1-{[(4S)-2,2-dimethyl-1,3-dioxolan-4-yl]methyl}cyclo propane sulfonate (S)-6

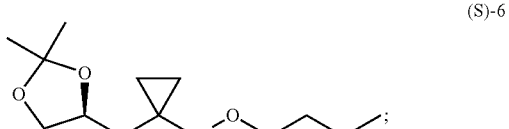

(S)-6 for preparing the compound of formula (S)-14, supra.

In an embodiment of said third aspect, the present invention relates to the use of:

Butyl 1-[(2S)-2,3-dihydroxypropyl]cyclopropanesulfonate (S)-5

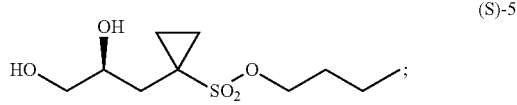 [SMILES: CCCCOS(=O)(=O)C1(C[C@H](O)CO)CC1]

(S)-5 for preparing the compound of formula (S)-14, supra.

In an embodiment of said third aspect, the present invention relates to the use of:

Butyl 1-[(2S)-oxiran-2-ylmethyl]cyclopropanesulfonate (S)-4

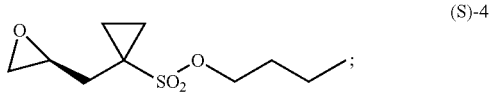

(S)-4 for preparing the compound of formula (S)-14, supra.

In an embodiment of said third aspect, the present invention relates to the use of:

Butyl 1-[(2S)-3-chloro-2-hydroxypropyl]cyclopropanesulfonate (S)-3

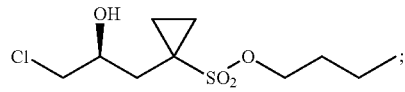

(S)-3 for preparing the compound of formula (S)-14, supra.

In an embodiment of said third aspect, the present invention relates to the use of:

Butyl 1-[(2S)-3-{[tert-butyl(dimethyl)silyl]oxy}-2-hydroxypropyl]cyclopropane-sulfonate (S)-9a

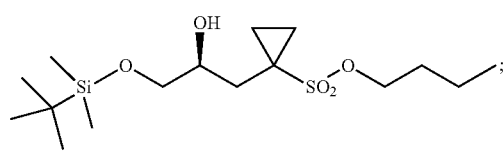

(S)-9a is for preparing the compound of formula (S)-14, supra.

In an embodiment of said third aspect, the present invention relates to the use of:

Butyl 1-[(2S)-2-hydroxy-3-(tetrahydro-2H-pyran-2-yloxy)propyl]cyclopropane sulfonate (S)-9b

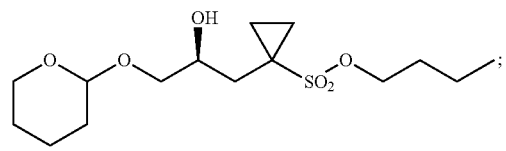

(S)-9b for preparing the compound of formula (S)-14, supra.

In a fourth aspect, the present invention relates to a method of preparing N-{3,4-difluoro-2-[(2-fluoro-4-iodophenyl)amino]-6-methoxyphenyl}-1-[(2R)-2,3-dihydroxy-propyl]cyclopropanesulfonamide of formula (R)-14:

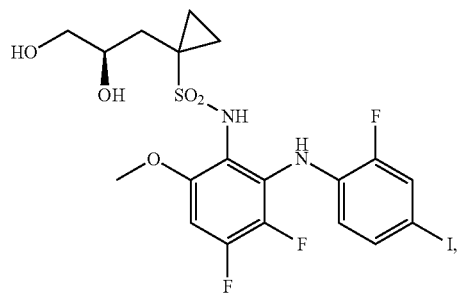

(R)-14 via the following steps shown in Schemes C and D, infra:

SCHEME C

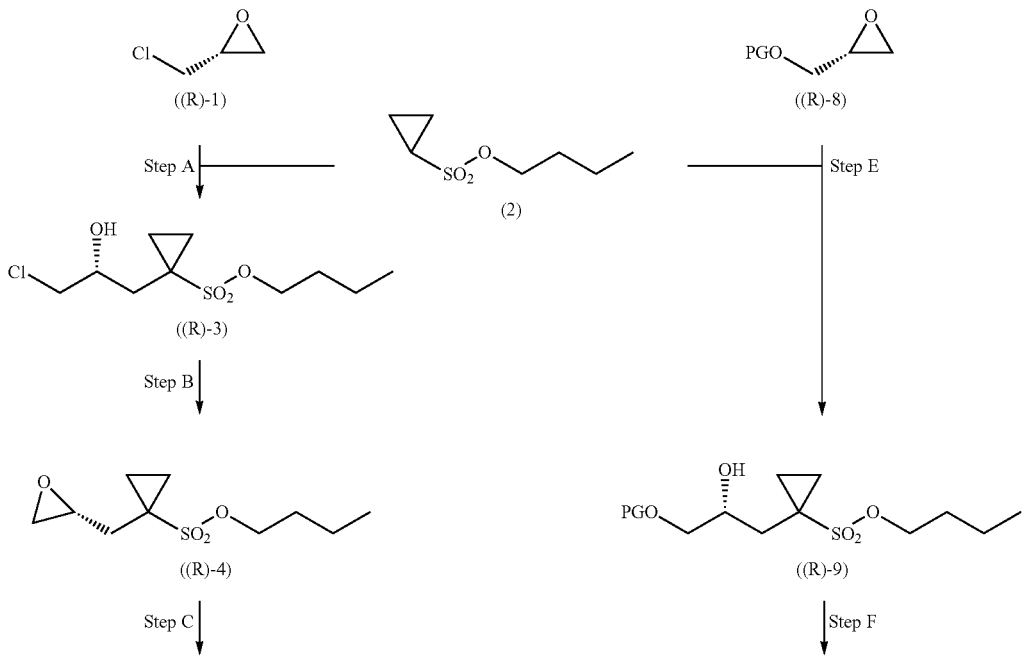

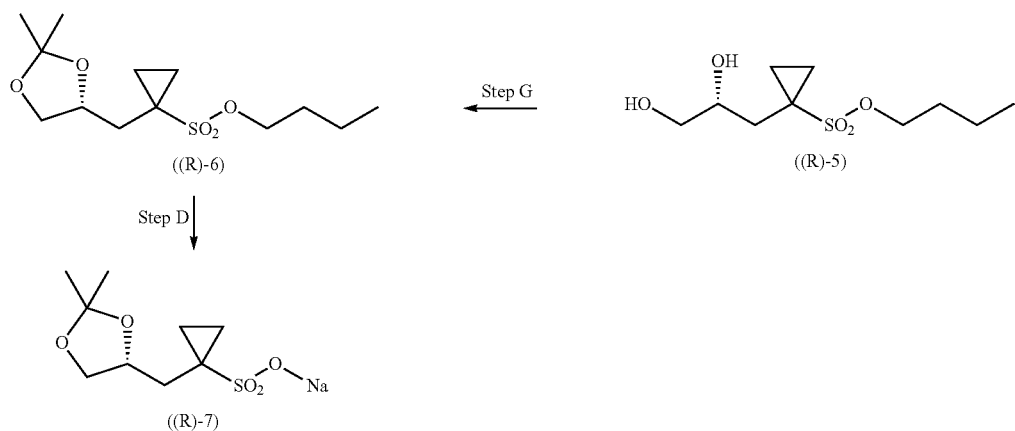
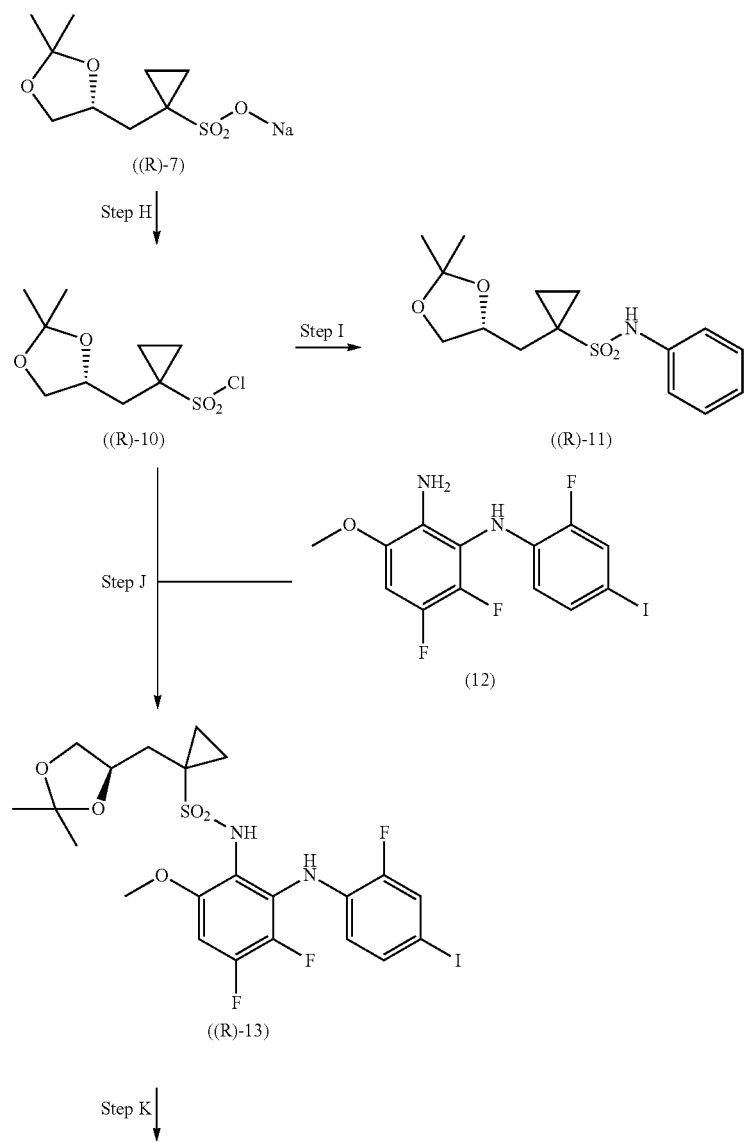
SCHEME D

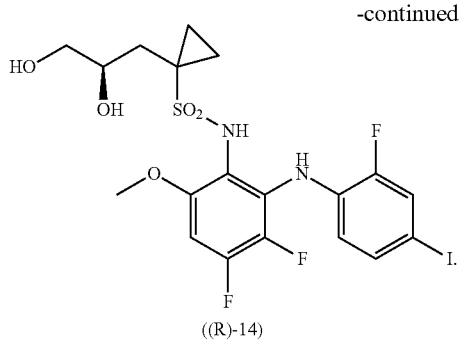

((R)-14)

In a further embodiment of the fourth aspect, the present invention relates to a method of preparing the compound of formula (R)-14, wherein each of said steps A to K as shown in Schemes C and D, supra, are described in analogy to the preparation of (S)-14 in Schemes A and B, and Schemes 3 to 9, supra.

In an embodiment of the fourth aspect, the present invention relates to a method of preparing a compound of formula (R)-14:

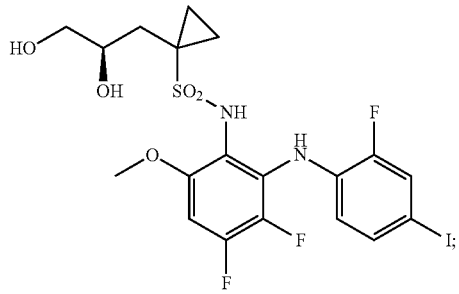

(R)-14 comprising:
i) the following step J:
wherein a compound of formula (R)-10:

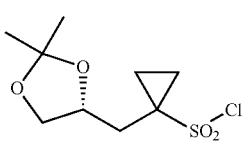

(R)-10 is allowed to react with a compound of formula (12):

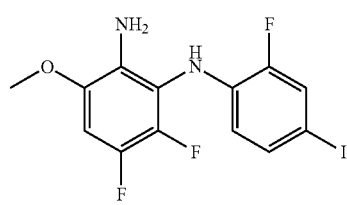

(12)

in the presence of a bromide, such as tetra-n-butylammonium bromide or lithium bromide for example, optionally in the presence of a base, such as pyridine for example, optionally in a solvent, such as sulfolane for example, thereby providing a reaction mixture containing a compound of formula (R)-13:

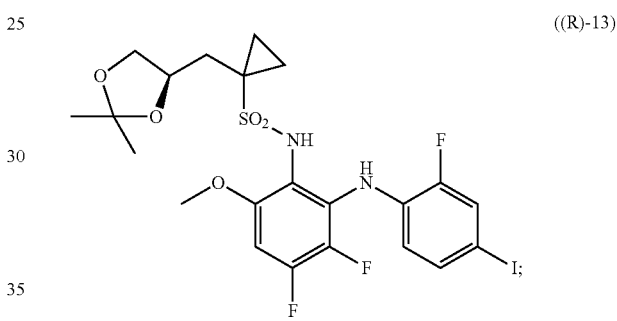

((R)-13)

and, then,
ii) the following step K:
wherein an aqueous mineral acid, such as hydrochloric acid for example, is added to said reaction mixture containing a compound of formula (R)-13,
thereby providing a compound of formula (R)-14.

Alternatively, in the above-mentioned step J, a catalyst, such as 4-dimethylaminopyridine for example, can be used instead of said bromide.

Alternatively, in scheme D, step J, the compound of formula (R)-10-Br:

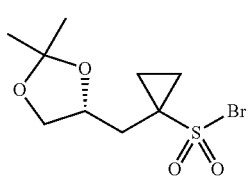

(R)-10-Br may be used instead of the compound (R)-10.

Hence, in an embodiment of the fourth aspect, the present invention relates to a method of preparing a compound of formula (R)-14:

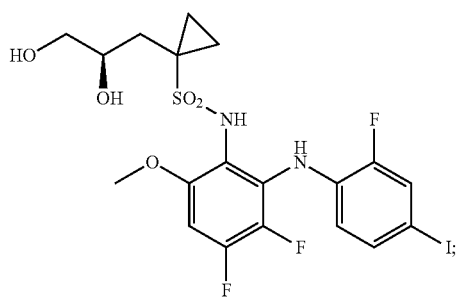

(R)-14 is comprising:
i) the following step J:
wherein a compound of formula (R)-10-Br:

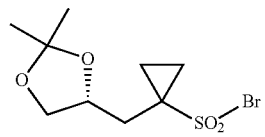

(R)-10-Br is allowed to react with a compound of formula (12):

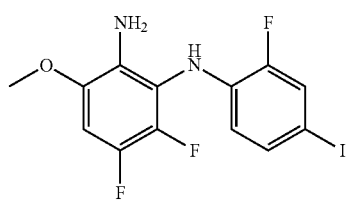

(12)

optionally in the presence of a base, such as pyridine for example, optionally in a solvent, such as sulfolane for example,
thereby providing a reaction mixture containing a compound of formula (R)-13:

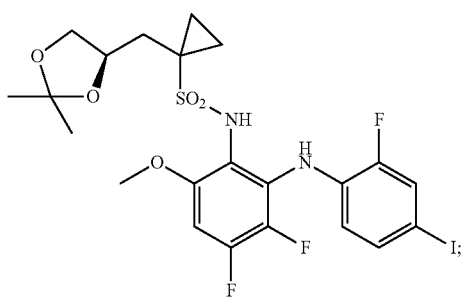

((R)-13)

and, then,
ii) the following step K:
wherein an aqueous mineral acid, such as hydrochloric acid for example, is added to said reaction mixture containing a compound of formula (R)-13,
thereby providing a compound of formula (R)-14.

In another embodiment of the fourth aspect, the present invention relates to a method of preparing a compound of formula (R)-14:

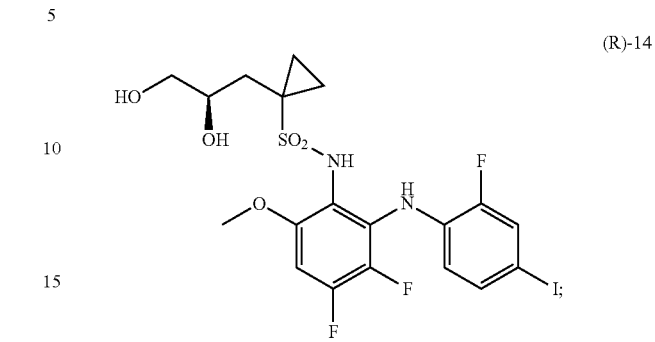

(R)-14 comprising the following step K:
wherein an aqueous mineral acid, such as hydrochloric acid for example, is added to a compound of formula (R)-13:

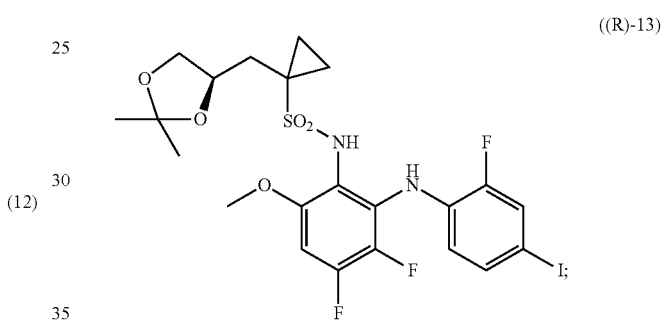

((R)-13)

thereby providing a compound of formula (R)-14.
In a further embodiment of the fourth aspect of the present invention, the above-mentioned compound of formula (R)-13:

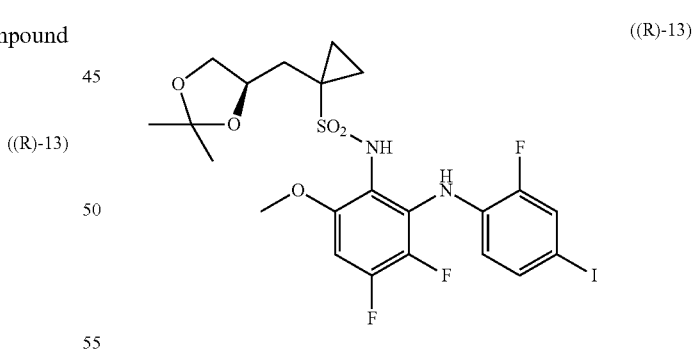

((R)-13)

is prepared by the following step J:
wherein a compound of formula (R)-10:

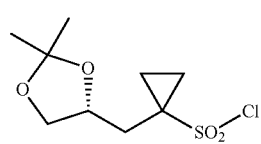

(R)-10 is allowed to react with a compound of formula (12):

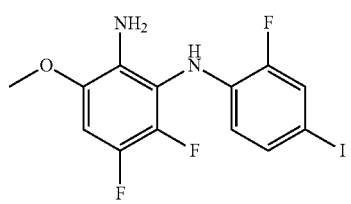
(12)

in the presence of a bromide, such as tetra-n-butylammonium bromide or lithium bromide for example, optionally in the presence of a base, such as pyridine for example, optionally in a solvent, such as sulfolane for example,
thereby providing a reaction mixture containing a compound of formula (R)-13:

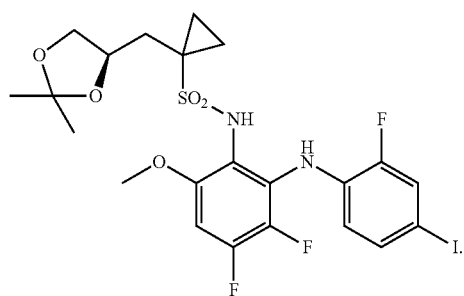
((R)-13)

Alternatively, in the above-mentioned step J, a catalyst, such as 4-dimethylaminopyridine for example, can be used instead of said bromide.

In a further embodiment of the fourth aspect of the present invention, the above-mentioned compound of formula (R)-13:

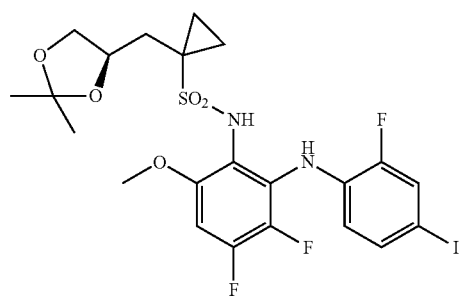
((R)-13)

is prepared by the following step J:
wherein a compound of formula (R)-10-Br:

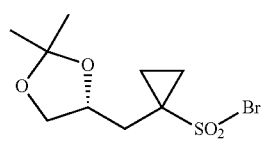
(R)-10-Br is allowed to react with a compound of formula (12):

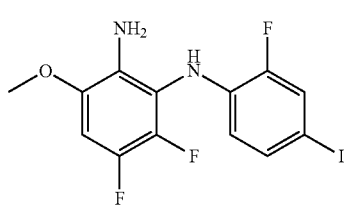
(12)

optionally in the presence of a base, such as pyridine for example, optionally in a solvent, such as sulfolane for example,
thereby providing a reaction mixture containing a compound of formula (R)-13:

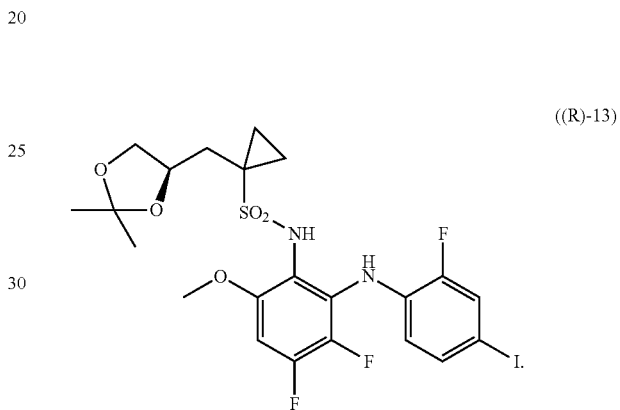
((R)-13)

In a further embodiment of the fourth aspect of the present invention, the above-mentioned compound of formula (R)-10:

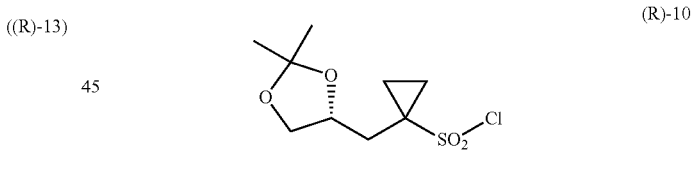
(R)-10 is prepared by allowing a compound of formula (R)-7:

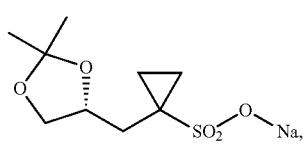
(R)-7 to react with a chlorinating agent, such as P(O)Cl$_3$, PCl$_3$ or SOCl$_2$ for example, optionally in a solvent, such as pyridine for example, thereby providing a compound of formula (R)-10.

In a further embodiment of the fourth aspect of the present invention, the above-mentioned compound of formula (R)-10-Br:

wherein a compound of formula (R)-7':

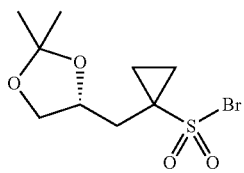
(R)-10-Br is prepared by allowing a compound of formula (R)-7:

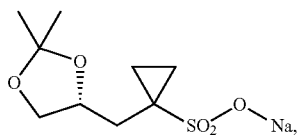
(R)-7 to react with a brominating agent, such as P(O)Br₃ or PBr₃ for example, optionally in a solvent, such as pyridine for example, thereby providing a compound of formula (R)-10-Br.

In a further embodiment of the fourth aspect of the present invention, the above-mentioned compound of formula (R)-7:

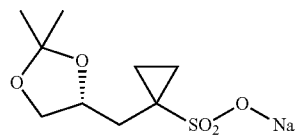
(R)-7 is prepared by allowing a compound of formula (R)-6:

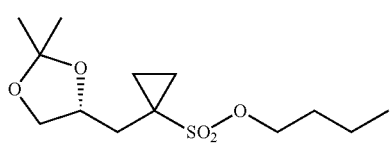
(R)-6 to react with a sodium alkoxide, such as sodium methoxide for example, optionally in a solvent, such as methanol for example, thereby providing a compound of formula (R)-7.

In a further embodiment of the fourth aspect, the present invention relates to a method of preparing a compound of formula (R)-10:

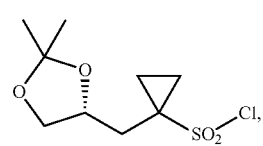
(R)-10

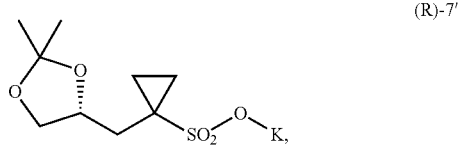
(R)-7' is allowed to react with a chlorinating agent, such as P(O)Cl₃, PCl₃ or SOCl₂ for example, optionally in a solvent, such as pyridine for example, thereby providing a compound of formula (R)-10.

In a further embodiment of the fourth aspect of the present invention, the above-mentioned compound of formula (R)-7':

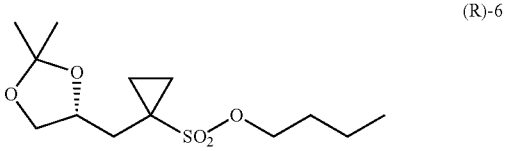
(R)-7' is prepared by allowing a compound of formula (R)-6:

(R)-6 to react with a potassium alkoxide, such as potassium methoxide for example, optionally in a solvent, such as methanol for example, thereby providing a compound of formula (R)-7'.

A further embodiment of the fourth aspect of the present invention relates to a method of preparing N-{3,4-difluoro-2-[(2-fluoro-4-iodophenyl)amino]-6-methoxyphenyl}-1-[(2R)-2,3-dihydroxy-propyl]cyclopropanesulfonamide of formula (R)-14:

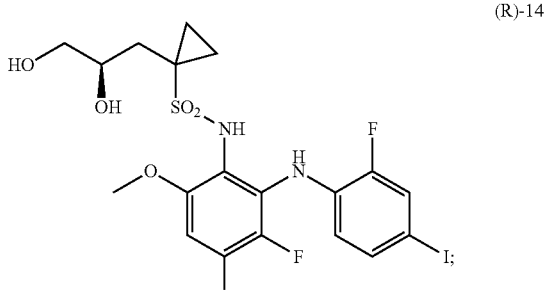
(R)-14 comprising the following step D:
wherein a compound of formula (R)-6:

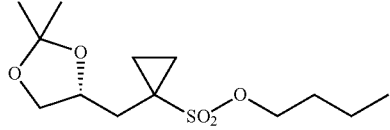

(R)-6 is allowed to react with a sodium alkoxide, such as sodium methoxide for example, optionally in a solvent, such as methanol for example, thereby providing a compound of formula (R)-7:

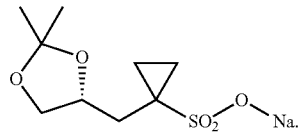

(R)-7

A further embodiment of the fourth aspect of the present invention relates to a method of preparing N-{3,4-difluoro-2-[(2-fluoro-4-iodophenyl)amino]-6-methoxyphenyl}-1-[(2R)-2,3-dihydroxy-propyl]cyclopropanesulfonamide of formula (R)-14:

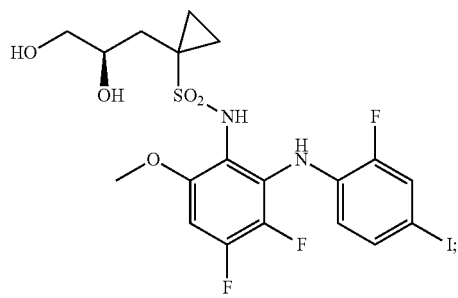

(R)-14 comprising the following step D:
wherein a compound of formula (R)-6:

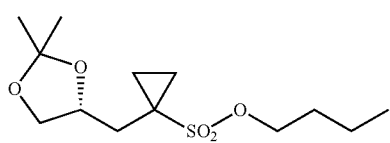

(R)-6 is allowed to react with a potassium alkoxide, such as potassium methoxide for example, optionally in a solvent, such as methanol for example, thereby providing a compound of formula (R)-7':

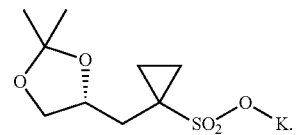

(R)-7'

In a further embodiment of the fourth aspect of the present invention, the above-mentioned compound of formula (R)-6:

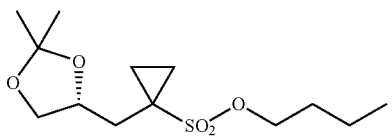

(R)-6 is prepared by allowing a compound of formula (R)-4:

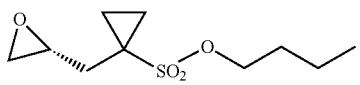

(R)-4 to react with either:
a) boron trifluoride, optionally in the form of a complex, such as a boron trifluoride etherate complex for example, such as a boron trifluoride tetrahydrofuran complex, or a boron trifluoride diethylether complex for example, optionally in a solvent such as acetone for example, or
b) phosphomolybdic acid hydrate, optionally in a solvent such as acetone for example,
thereby providing a compound of formula (R)-6.

In a further embodiment of the fourth aspect of the present invention, the above-mentioned compound of formula (R)-4:

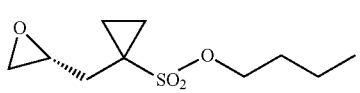

(R)-4 is prepared by allowing a compound of formula (R)-3:

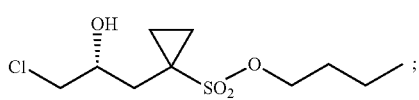

(R)-3 to react with a base, such as sodium hydroxide for example, optionally in a solvent, such as water for example,
thereby providing a compound of formula (R)-4.

In a further embodiment of the fourth aspect of the present invention, the above-mentioned compound of formula (R)-3:

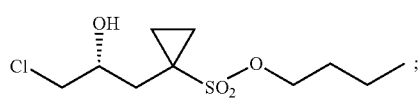
(R)-3 is prepared by:
a) allowing a compound of formula 2:

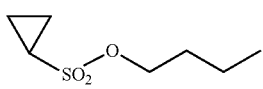
(2)

to react with a base, such as n-butyllithium for example, optionally in a solvent, such as tetrahydrofuran for example,
b) adding a compound of formula (R)-1 and boron trifluoride, optionally in the form of a complex, such as a boron trifluoride etherate complex for example, such as a boron trifluoride tetrahydrofuran complex, or a boron trifluoride diethylether complex for example; and
c) allowing the thus-formed deprotonated compound of formula 2 to react with a compound of formula (R)-1:

(R)-1 thereby providing a compound of formula (R)-3.

In a further embodiment of the fourth aspect of the present invention, the above-mentioned compound of formula (R)-6:

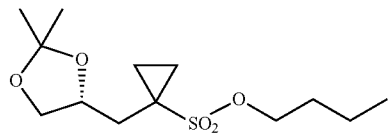
(R)-6 is prepared by allowing a compound of formula (R)-5:

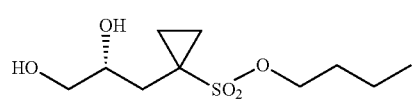
(R)-5 to react with 2,2-dimethoxypropane, optionally in a solvent, such as tetrahydrofuran for example and optionally in the presence of a catalyst, such as pyridinium p-toluenesulfonate for example,
thereby providing a compound of formula (R)-6.

In a further embodiment of the fourth aspect of the present invention, the above-mentioned compound of formula (R)-5:

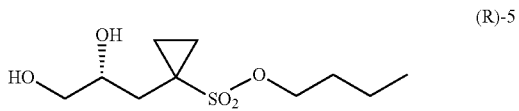
(R)-5 is prepared by allowing a compound of formula (R)-9:

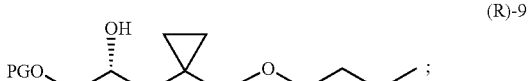
(R)-9 wherein PG represents a protecting group, such as a t-butyldimethylsilyl- group (compound (R)-9a) or a tetrahydropyranyl group (compound (R)-9b), for example,
to react with an acid, such as hydrochloric acid or p-toluene sulfonic acid for example, optionally in a solvent, such as methanol for example,
thereby providing a compound of formula (R)-5.

In a further embodiment of the fourth aspect of the present invention, the above-mentioned compound of formula (R)-9:

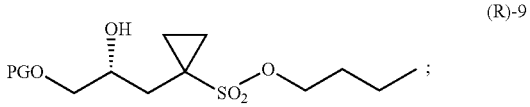
(R)-9 wherein PG represents a t-butyldimethylsilyl- group (compound (R)-9a) or a tetrahydropyranyl group (compound (R)-9b),
is prepared by:
a) allowing a compound of formula 2:

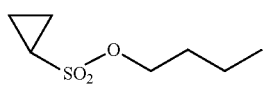
(2)

to react with a base, such as n-butyllithium for example, optionally in a solvent, such as tetrahydrofuran for example,
b) adding a compound of formula (R)-8 and boron trifluoride, optionally in the form of a complex, such as a boron trifluoride etherate complex for example, such as a boron trifluoride tetrahydrofuran complex, or a boron trifluoride diethylether complex for example; and
c) allowing the thus-formed deprotonated compound of formula 2 to react with a compound of formula (R)-8:

(R)-8 wherein PG represents a t-butyldimethylsilyl- group (compound (R)-8a) or a tetrahydropyranyl group (compound (R)-8b), respectively,
thereby providing a compound of formula (R)-9.

In a further embodiment of the fourth aspect, the present invention relates to a method of preparing the compound of formula (R)-14, wherein each of said steps A to K as shown in Schemes C and D, supra, are described in relation to Schemes 3 to 9, supra.

In accordance with a fifth aspect, the present invention relates to intermediate compounds which are useful in the preparation of the above-mentioned compound of formula (R)-14.

In an embodiment of said fifth aspect, the present invention relates to a compound:

1-{[(4R)-2,2-dimethyl-1,3-dioxolan-4-yl]methyl}cyclopropanesulfonyl bromide (R)-10-Br

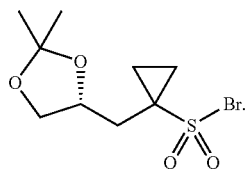
(R)-10-Br

In an embodiment of said fifth aspect, the present invention relates to a compound:

potassium 1-{[(4R)-2,2-dimethyl-1,3-dioxolan-4-yl]methyl}cyclopropane-sulfonate (R)-7'

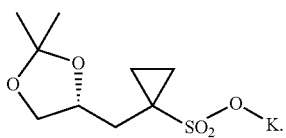
(R)-7'

In an embodiment of said fifth aspect, the present invention relates to a compound:

Butyl 1-{[(4R)-2,2-dimethyl-1,3-dioxolan-4-yl]methyl}cyclo propane sulfonate (R)-6

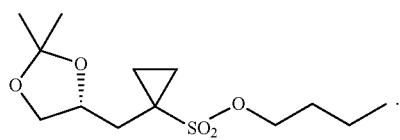
(R)-6

In an embodiment of said fifth aspect, the present invention relates to a compound:

Butyl 1-[(2R)-2,3-dihydroxypropyl]cyclopropanesulfonate (R)-5

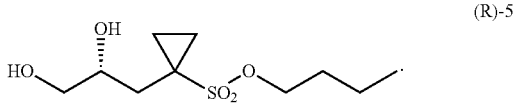
(R)-5

In an embodiment of said fifth aspect, the present invention relates to a compound:

Butyl 1-[(2R)-oxiran-2-ylmethyl]cyclopropanesulfonate (R)-4

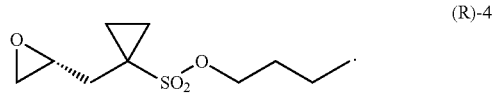
(R)-4

In an embodiment of said fifth aspect, the present invention relates to a compound:

Butyl 1-[(2R)-3-chloro-2-hydroxypropyl]cyclopropanesulfonate (R)-3

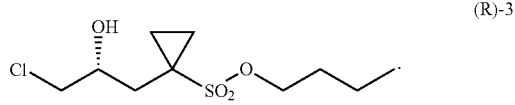 [SMILES: CCCCOS(=O)(=O)C1(C[C@@H](O)CCl)CC1]
(R)-3

In an embodiment of said fifth aspect, the present invention relates to a compound:

Butyl 1-[(2R)-3-{[tert-butyl(dimethyl)silyl]oxy}-2-hydroxypropyl]cyclopropane-sulfonate (R)-9a

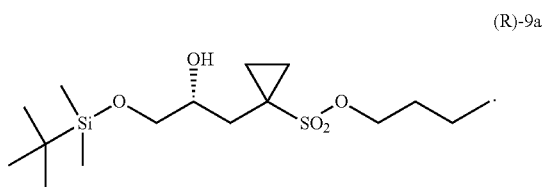 [SMILES: CCCCOS(=O)(=O)C1(C[C@@H](O)CO[Si](C)(C)C(C)(C)C)CC1]
(R)-9a

In an embodiment of said fifth aspect, the present invention relates to a compound:

Butyl 1-[(2R)-2-hydroxy-3-(tetrahydro-2H-pyran-2-yloxy)propyl]cyclopropane sulfonate (R)-9b

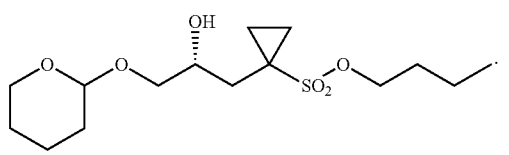
(R)-9b

In a sixth aspect, the present invention relates to the use of the intermediate compounds according to the fifth aspect, supra, for preparing the compound of formula (R)-14, supra.

In an embodiment of said sixth aspect, the present invention relates to the use of:

1-{[(4R)-2,2-dimethyl-1,3-dioxolan-4-yl]methyl}cyclopropanesulfonyl bromide (R)-10-Br

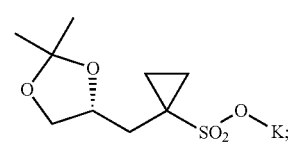
(R)-10-Br for preparing the compound of formula (R)-14, supra.

In an embodiment of said sixth aspect, the present invention relates to the use of:

potassium 1-{[(4R)-2,2-dimethyl-1,3-dioxolan-4-yl]methyl}cyclopropane-sulfonate (R)-7'

(R)-7' for preparing the compound of formula (R)-14, supra.

In an embodiment of said sixth aspect, the present invention relates to the use of:

Butyl 1-{[(4R)-2,2-dimethyl-1,3-dioxolan-4-yl]methyl}cyclo propane sulfonate (R)-6

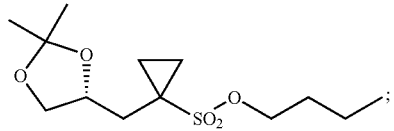
(R)-6 for preparing the compound of formula (R)-14, supra.

In an embodiment of said sixth aspect, the present invention relates to the use of:

Butyl 1-[(2R)-2,3-dihydroxypropyl]cyclopropanesulfonate (R)-5

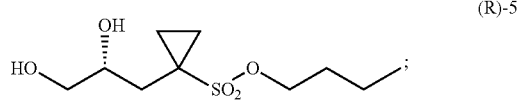 [SMILES: CCCCOS(=O)(=O)C1(C[C@@H](O)CO)CC1]
(R)-5 for preparing the compound of formula (R)-14, supra.

In an embodiment of said sixth aspect, the present invention relates to the use of:

Butyl 1-[(2R)-oxiran-2-ylmethyl]cyclopropanesulfonate (R)-4

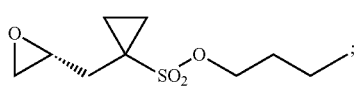
(R)-4 for preparing the compound of formula (R)-14, supra.

In an embodiment of said sixth aspect, the present invention relates to the use of:

Butyl 1-[(2R)-3-chloro-2-hydroxypropyl]cyclopropanesulfonate (R)-3

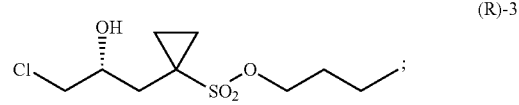 [SMILES: CCCCOS(=O)(=O)C1(C[C@@H](O)CCl)CC1]
(R)-3 for preparing the compound of formula (R)-14, supra.

In an embodiment of said sixth aspect, the present invention relates to the use of:

Butyl 1-[(2R)-3-{[tert-butyl(dimethyl)silyl]oxy}-2-hydroxypropyl]cyclopropane-sulfonate (R)-9a

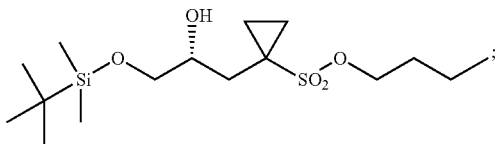

(R)-9a for preparing the compound of formula (R)-14, supra.

In an embodiment of said sixth aspect, the present invention relates to the use of:

Butyl 1-[(2R)-2-hydroxy-3-(tetrahydro-2H-pyran-2-yloxy)propyl]cyclopropane sulfonate (R)-9b (R)-9b for preparing the compound of formula (R)-14, supra.

Within the context of the present invention the term "solvent", as optionally present in any reaction step of the method of the invention, is understood, as is by the person skilled in the art, as meaning any substance in which other materials dissolve to form a solution, such as, without being limited to: a polar solvent, such as a polar protic solvent, such as water, n-butanol, isopropanol, n-propanol, ethanol, methanol, or formic acid or acetic acid, etc., for example; a polar aprotic solvent, such as 1,4-dioxane, tetrahydrofuran, 1,2-dimethoxyethane, acetone, acetonitrile, dimethylformamide, sulfolane, pyridine or dimethylsulphoxide, etc., for example; or a non-polar solvents, such as pentane, hexane, benzene, toluene, diethyl ether, methyl ethyl ketone, dichloromethane, chloroform, tetrachloromethane, ethyl acetate, etc., for example; or any mixture of the solvents listed above.

It is understood that any combination of the definitions given in the above-mentioned embodiments is possible within the context of the present invention.

The invention will be better understood upon reading the Examples below, which are provided as an illustration of the present invention. The Examples below in no way whatsoever constitute a limitation of the present invention as described in the present text and as defined in the claims appended hereto.

EXPERIMENTAL SECTION

Examples

Abbreviations Used

The following abbreviations used in the Examples have the following meanings:
TMEDA N,N,N',N'-Tetramethylethylenediamine
DMI 1,3-Dimethyl-2-imidazolidinone
DMPU 1,3-Dimethyl-3,4,5,6-tetrahydro-2(1H)-pyrimidinone
conc. concentrated
h hour/hours
THF tetrahydrofuran
1H-NMR proton nuclear magnetic resonance spectroscopy: chemical shifts (δ) are given in ppm.
s singlet
bs broad singlet
d doublet
dd doublet of doublets
t triplet General Butyl cyclopropanesulfonate 2 and 5,6-difluoro-N1-(4-fluoro-2-iodophenyl)-3-methoxybenzene-1,2-diamine can be prepared as described in [ref. 2, Example 12, Step B, and Example 50, Step B, respectively]. All other reagents are commercially available.

Example 1

General Procedure for the synthesis of substituted Butyl 1-[2-hydroxypropyl]cyclopropanesulfonates (GP1)

A solution of butyl cyclopropanesulfonate 2 (1.2 g, 6.7 mmol) in THF (24 mL) was cooled to −78° C. and n-butyllithium (1.6M in n-hexane, 5.0 mL, 8.1 mmol) was added within 5 min. The mixture was stirred for 30 min and epoxypropane derivative 1 or 8 (8.1 mmol) was added followed by addition of boron trifluoride diethyl etherate (0.84 mL, 6.7 mmol). The solution was stirred for 1 h at −78° C., the cooling bath was removed and stirring was continued for 2 additional hours. For aqueous work-up diluted hydrochloric acid (10%, 0.8 mL), water (10 mL) and ethyl acetate (20 mL) were added. The organic layer was is concentrated at 40° C. to afford the corresponding butyl 1-[2-hydroxypropyl]cyclopropanesulfonate 3.

According to GP1 the following compounds were prepared:

Example 1a

Butyl 1-[(2S)-3-chloro-2-hydroxypropyl]cyclopropanesulfonate (S)-3

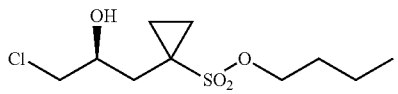

(S)-3 was obtained from (S)-epichlorohydrin (S)-1 in 81.3% yield.

$R_f$: 0.19 (silica gel, n-hexane/ethyl acetate 3:1)

MS (DCI): m/z=288.0 [M+NH$_4$]$^+$ (100), 271 [M+H]$^+$ (14)

$^1$H NMR (400 MHz, Chloroform-d) δ=0.90-1.04 (m, 4H) 1.15-1.23 (m, 1H) 1.39-1.57 (m, 4H) 1.67-1.80 (m, 2H) 1.90

(dd, J=15.28, 8.68 Hz, 1H) 2.15 (dd, J=15.41, 3.67 Hz, 1H) 2.5-3.0 (br. s, 2H) 3.51-3.73 (m, 2H) 4.13-4.34 (m, 3H) ppm Example 1b Butyl 1-[(2R)-3-chloro-2-hydroxypropyl]cyclopropanesulfonate (R)-3

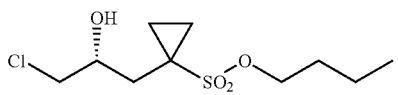 [SMILES: CCCCOS(=O)(=O)C1(CC(O)CCl)CC1]

(R)-3 was obtained from (R)-epichlorohydrin (R)-1 in 98.7% yield. Analytical data see (S)-3.

Example 1c

Butyl 1-[3-chloro-2-hydroxypropyl]cyclopropanesulfonate rac-3

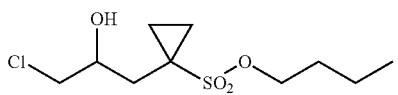

rac-3 was obtained from epichlorohydrin in 72.5% yield. Analytical data see (S)-3

Example 1d

Butyl 1-[(2S)-3-{[tert-butyl(dimethyl)silyl]oxy}-2-hydroxypropyl]cyclopropanesulfonate (S)-9a

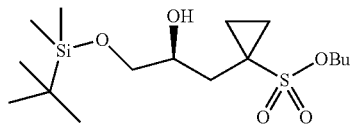

(S)-9a was prepared from tert-butyl(dimethyl)[(2S)-oxiran-2-ylmethoxy]silane in 100% yield (crude product).
$R_f$: 0.43 (silica gel, n-hexane/ethyl acetate 3:1)
GC-MS: m/z=384.1 [M+NH$_4$]$^+$ (100), 367.0 [M+H]$^+$ (8)
The crude product was converted without further purification to (S)-5

Example 1e

Butyl 1-[(2R)-3-{[tert-butyl(dimethyl)silyl]oxy}-2-hydroxypropyl]cyclopropanesulfonate (R)-9a

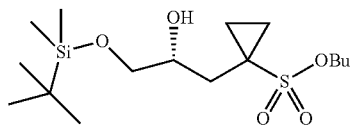

(R)-9a was prepared from tert-butyl(dimethyl)[(2R)-oxiran-2-ylmethoxy]silane in 100% yield (crude product).
GC-MS: 70% (R)-9a, 7% (R)-5
$R_f$: 0.43 (silica gel, n-hexane/ethyl acetate 3:1)
MS (DCI): m/z=384.0 [M+NH$_4$]$^+$ (34), 367.1 [M+H]$^+$ (38), 270.1 [M$_{(R)-2}$+NH$_4$]$^+$ (100)
The crude product was converted without further purification to (R)-5

Example 1f

Butyl 1-[(2R)-2-hydroxy-3-(tetrahydro-2H-pyran-2-yloxy)propyl]cyclopropanesulfonate (R)-9b

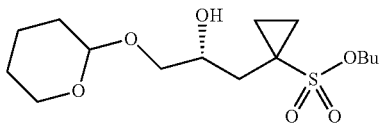

(R)-9b was prepared from 2-[(2R)-oxiran-2-ylmethoxy]tetrahydro-2H-pyran in 100% yield (crude product) and converted without purification to (R)-5
$R_f$: 0.29 (silica gel, n-hexane/ethyl acetate 3:1)
MS (DCI): m/z=354.0 [M+NH$_4$]$^+$ (5), 337.1 [M+H]$^+$ (4), 270.1 [M$_{(R)-2}$+NH$_4$]$^+$ (100), 253.1 [M$_{(R)-2}$+H]$^+$ (15)

Example 2

General Procedure for the Synthesis of Butyl 1-[oxiran-2-ylmethyl]cyclopropane-sulfonates 4 (GP2)

To a solution of 3 (22.1 mmol) in tetrahydrofuran (29 mL) was added a solution of sodium hydroxide (33.2 mmol) in water (22 mL) and the mixture was stirred overnight at room temperature to complete conversion (TLC silica gel, toluene/ethyl acetate 5:1). The reaction mixture was washed with ethyl acetate (30 mL), the organic layer was concentrated and the crude product purified by chromatography (silica gel, toluene/ethyl acetate 5:1). According to GP2 the following compounds were prepared:

Example 2a

Butyl 1-[(2S)-oxiran-2-ylmethyl]cyclopropanesulfonate (S)-4

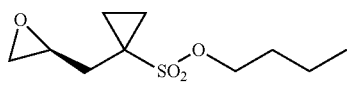

(S)-4 was obtained from (S)-3 in 85.0% yield
$R_f$: 0.40 (silica gel, toluene/ethyl acetate 5:1)
MS (DCI): m/z=252.1 [M+NH$_4$]$^+$ (100), 235.0 [M+H]$^+$ (10),
$^1$H NMR (400 MHz, Chloroform-d) δ=0.89-1.06 (m, 4H) 1.14-1.23 (m, 1H) 1.37-1.55 (m, 4H) 1.61-1.79 (m, 3H) 2.40

(m, J=15.28, 4.52 Hz, 1H) 2.48 (dd, J=4.89, 2.69 Hz, 1H) 2.76-2.85 (m, 1H) 3.14-3.23 (m, 1H) 4.25 (td, J=6.48, 0.98 Hz, 2H) ppm.

Example 2b

Butyl 1-[(2R)-oxiran-2-ylmethyl]cyclopropanesulfonate (R)-4

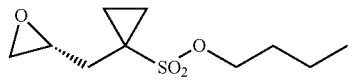

(R)-4 was obtained from (R)-3 in 86.3% yield. Analytical data see (S)-4

Example 2c

Butyl 1-[oxiran-2-ylmethyl]cyclopropanesulfonate rac-4

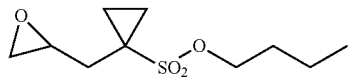

rac-4 was obtained from rac-3 in 92.5% yield. Analytical data see (S)-4

Example 3

General Procedure for the Synthesis of Butyl 1-[2,3-dihydroxypropyl]cyclopropane-sulfonates 5 by Acidic Deprotection of 9a To 9a (6.7 mmol) was added hydrochloric acid (10%, 4 ml) and methanol (24.5 mL) and it was stirred until TLC (silica gel, hexanes/ethyl acetate 3:1) indicated complete conversion (1 h). For aqueous work-up ethyl acetate (50 mL) was added and it was washed with a saturated aq. solution of sodium hydrogen carbonate (2×20 mL). The organic layer was concentrated and the residual oil was purified by chromatography (silica gel, 1. hexanes/ethyl acetate 3:1, 2. ethyl acetate).

According to GP3 the following compounds were prepared:

Example 3a

Butyl 1-[(2S)-2,3-dihydroxypropyl]cyclopropanesulfonate (S)-5

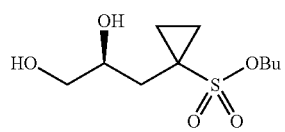

(S)-5 was obtained from (S)-9a in 97.1% yield $R_f$: 0.36 (silica gel, ethyl acetate);

MS (DCI): m/z=270.1 $[M+NH_4]^+$ (100), 253.1 $[M+H]^+$ (17)

$^1$H NMR (400 MHz, Chloroform-d) δ=0.90-1.03 (m, 4H) 1.12-1.19 (m, 1H) 1.38-1.54 (m, 4H) 1.68-1.79 (m, 2H) 1.84 (dd, J=15.41, 9.29 Hz, 1H) 2.00 (dd, J=15.41, 3.42 Hz, 1H) 2.55 (m, 1H) 3.23 (d, J=3.91 Hz, 1H) 3.47 (dt, J=11.37, 5.81 Hz, 1H) 3.60-3.72 (m, 1H) 4.11 (dt, J=6.11, 2.81 Hz, 1H) 4.25 (td, J=6.60, 1.47 Hz, 2H) ppm

Example 3b

Butyl 1-[(2R)-2,3-dihydroxypropyl]cyclopropanesulfonate (R)-5

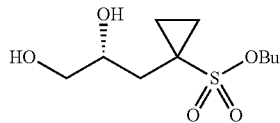

(R)-5 was obtained from (R)-9a in 88.2 yield.

$R_f$: 0.36 (silica gel, ethyl acetate);

MS (DCI): m/z=270.1 $[M+NH_4]^+$ (100), 253.1 $[M+H]^+$ (17)

$^1$H NMR (400 MHz, Chloroform-d) δ=0.90-1.03 (m, 4H) 1.12-1.19 (m, 1H) 1.38-1.54 (m, 4H) 1.68-1.79 (m, 2H) 1.84 (dd, J=15.41, 9.29 Hz, 1H) 2.00 (dd, J=15.41, 3.42 Hz, 1H) 2.55 (m, 1H) 3.23 (d, J=3.91 Hz, 1H) 3.47 (dt, J=11.37, 5.81 Hz, 1H) 3.60-3.72 (m, 1H) 4.11 (dt, J=6.11, 2.81 Hz, 1H) 4.25 (td, J=6.60, 1.47 Hz, 2H) ppm

Example 3c

Preparation of Butyl 1-[(2R)-2,3-dihydroxypropyl]cyclopropanesulfonate (R)-5 by Hydrolysis of (R)-9b

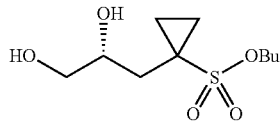

Crude (R)-9b (10 mmol) was dissolved in methanol (38 mL), p-toluene sulfonic acid (30 mg) was added and stirring was continued for 5.5 h until the reaction was completed (TLC, silica gel, ethyl acetate). The mixture was concentrated and the residue purified by chromatography (silica gel, ethyl acetate) to yield a colorless oil.

Yield: 1.1 g, 40.4%

$R_f$: 0.36 (silica gel, ethyl acetate);

MS (DCI): m/z=270.1 $[M+NH_4]^+$ (100), 253.1 $[M+H]^+$ (17)

$^1$H NMR (400 MHz, Chloroform-d) δ=0.90-1.03 (m, 4H) 1.12-1.19 (m, 1H) 1.38-1.54 (m, 4H) 1.68-1.79 (m, 2H) 1.84 (dd, J=15.41, 9.29 Hz, 1H) 2.00 (dd, J=15.41, 3.42 Hz, 1H) 2.55 (m, 1H) 3.23 (d, J=3.91 Hz, 1H) 3.47 (dt, J=11.37, 5.81

Hz, 1H) 3.60-3.72 (m, 1H) 4.11 (dt, J=6.11, 2.81 Hz, 1H) 4.25 (td, J=6.60, 1.47 Hz, 2H) ppm

Example 4

General Procedure for the Synthesis of Butyl 1-{[2,2-dimethyl-1,3-dioxolan-4-yl]methyl}-cyclopropanesulfonates 6 from diols 5

To a solution of 5 (0.6 g, 4.0 mmol) in THF (2.4 mL) was added 2,2-dimethoxypropane (1.5 ml, 11.9 mmol) and pyridinium p-toluenesulfonate (29.9 mg, 0.1 mmol). It was stirred until complete conversion overnight (TLC, silica gel, ethyl acetate). Ethyl acetate (20 mL) and a saturated aq. solution of sodium hydrogen carbonate (10 mL) were added; the organic layer was washed with brine (10 mL), dried over magnesium sulfate and concentrated at 40° C. The residue was purified by chromatography (silica gel, hexane/ethyl acetate 3:1).

Example 4a

Butyl 1-{[(4S)-2,2-dimethyl-1,3-dioxolan-4-yl]methyl}cyclopropanesulfonate (S)-6

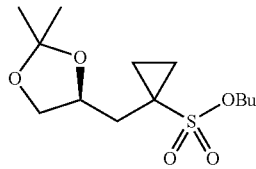

(S)-6 was obtained from (S)-5 in 84.1% yield.
$R_f$: 0.40 (silica gel, n-hexane/ethyl acetate 3:1)
MS (DCI): m/z=310.1 [M+NH$_4$]$^+$ (27), 293.0 [M+H]$^+$ (100), 277.0 (6), 235.0 (14), 196.0 (3)
$^1$H NMR (500 MHz, Chloroform-d) δ=0.83-0.96 (m, 4H) 1.12-1.20 (m, 1H) 1.27 (s, 3H) 1.31 (s, 3H) 1.33-1.44 (m, 4H) 1.62-1.70 (m, 2H) 1.75 (dd, J=15.11, 8.32 Hz, 1H) 2.27 (dd, J=15.15, 4.31 Hz, 1H) 3.46 (dd, J=8.05, 6.98 Hz, 1H) 4.05 (dd, J=8.16, 6.10 Hz, 1H) 4.12-4.22 (m, 2H) 4.28-4.39 (m, 1H) ppm

Example 4b

Butyl 1-{[(4R)-2,2-dimethyl-1,3-dioxolan-4-yl]methyl}cyclopropanesulfonate (R)-6

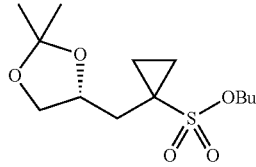

(R)-6 was obtained from (R)-5 in 74.8% yield.
$R_f$: 0.40 (silica gel, n-hexane/ethyl acetate 3:1)
MS (DCI): m/z=310.1 [M+NH$_4$]$^+$ (27), 293.0 [M+H]$^+$ (100), 277.0 (6), 235.0 (14), 196.0 (3)
$^1$H NMR (500 MHz, Chloroform-d) δ=0.83-0.96 (m, 4H) 1.12-1.20 (m, 1H) 1.27 (s, 3H) 1.31 (s, 3H) 1.33-1.44 (m, 4H) 1.62-1.70 (m, 2H) 1.75 (dd, J=15.11, 8.32 Hz, 1H) 2.27 (dd, J=15.15, 4.31 Hz, 1H) 3.46 (dd, J=8.05, 6.98 Hz, 1H) 4.05 (dd, J=8.16, 6.10 Hz, 1H) 4.12-4.22 (m, 2H) 4.28-4.39 (m, 1H) ppm

Example 5

General Procedure for the Synthesis of Butyl 1-{[2,2-dimethyl-1,3-dioxolan-4-yl]methyl}-cyclopropanesulfonates 6 directly from epoxides 4 (GP4)

According to GP4 the following compounds were prepared:

Example 5a i)

Synthesis of Butyl 1-{[(4R)-2,2-dimethyl-1,3-dioxolan-4-yl]methyl}cyclopropanesulfonate (R)-6 from Epoxide (R)-4

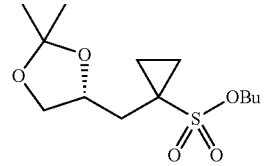

To a solution of (R)-4 (12.5 g, 53.3 mmol) in 115 mL acetone was added boron trifluoride diethyl etherate (1.8 g, 12.8 mmol). The solution was stirred for 2 h at room temperature. Ethyl acetate (235 mL) and sat. aq. sodium carbonate (235 mL) were added, the organic layer was separated and concentrated in vacuum. The residue was dissolved in ethyl acetate (250 mL) and washed twice with water (50 mL each). The organic layer was concentrated in vacuum.
Yield: 15.3 g, 98.1%
Optical purity: 58.2% ee (determined by chiral HPLC of the corresponding anilide (R)-11)

Example 5a ii)

Synthesis of Butyl 1-{[(4R)-2,2-dimethyl-1,3-dioxolan-4-yl]methyl}cyclopropanesulfonate (R)-6 from (R)-4

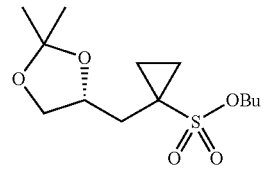

To a solution of (R)-4 (0.6 g g 2.5 mmol) in 5 mL acetone was added phosphomolybdic acid hydrate (50 mg, 0.03 mmol). It was stirred for 2 h at room temperature until TLC (silica gel, ethyl acetate) indicated complete conversion. The crude product was purified by chromatography (silica gel, ethyl acetate) to furnish an oil.
Yield: 0.65 g, 86.8%
Optical purity: 69.8% ee (determined by chiral HPLC of the corresponding anilide (R)-11)

Example 6

General Procedure for the Synthesis of Sodium 1-{[2,2-dimethyl-1,3-dioxolan-4-yl]methyl}-cyclopropanesulfonates 7 (GP5)

To a solution of 6 (0.5 g, 1.7 mmol) in 1,2-dimethoxyethane (3.3 mL) was added a solution of sodium methoxide (30% in methanol, 0.49 mL, 2.6 mmol). It was stirred under reflux temperature until complete conversion (TLC, silica gel, ethyl acetate) (1.5 h) and concentrated at 45° C. to yield a solid. The solid was stirred with hexanes (5 mL), isolated by filtration, crystallized from ethanol (3.5 mL per g) or isopropanol (8.0 mL per g) under reflux temperature and dried in vacuo at 45° C.

According to GP5 the following compounds were prepared:

Example 6a

Sodium 1-{[(4S)-2,2-dimethyl-1,3-dioxolan-4-yl]methyl}cyclopropanesulfonate (S)-7

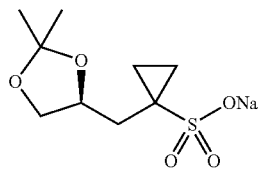

(S)-7 was obtained from (S)-6 in quantitative yield.
MS: m/z=281.0 [M+Na]$^+$
$^1$H NMR (400 MHz, DMSO-$d_6$) δ=0.36-0.50 (m, 2H) 0.78-0.90 (m, 2H) 1.23 (s, 3H) 1.26 (s, 3H) 1.69 (dd, J=14.18, 7.58 Hz, 1H) 1.91-2.01 (m, 1H) 3.48 (t, J=7.70 Hz, 1H) 4.02 (dd, J=7.82, 5.87 Hz, 1H) 4.44 (s, 1H) ppm Optical purity: >99.9% ee
(obtained from (S)-8 via steps E, F, G, D (cf. Scheme 1 supra)
(determined by chiral HPLC of the corresponding anilide (S)-11)

Example 6b

Sodium 1-{[(4R)-2,2-dimethyl-1,3-dioxolan-4-yl]methyl}cyclopropanesulfonate (R)-7

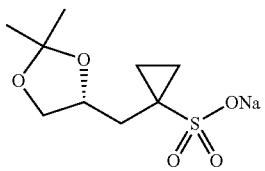

(R)-7 was obtained from (R)-6 in quantitative yield.
MS: m/z=281.0 [M+Na]$^+$
$^1$H NMR (400 MHz, DMSO-$d_6$) δ=0.36-0.50 (m, 2H) 0.78-0.90 (m, 2H) 1.23 (s, 3H) 1.26 (s, 3H) 1.69 (dd, J=14.18, 7.58 Hz, 1H) 1.91-2.01 (m, 1H) 3.48 (t, J=7.70 Hz, 1H) 4.02 (dd, J=7.82, 5.87 Hz, 1H) 4.44 (s, 1H) ppm Optical purity: 99.4% ee (R)-7 obtained from (R)-8a
99.7% ee (R)-7 obtained from (R)-8b
(determined by chiral HPLC of the corresponding anilide (R)-11)

Example 7

General Procedures for the Synthesis of 1-{[2,2-dimethyl-1,3-dioxolan-4-yl]methyl}cyclopropanesulfonyl chlorides 10 (GP6a and GP6b)

GP6a:
To a suspension of 7 (0.50 g, 1.9 mmol) in 5 mL pyridine was added under cooling phosphoric trichloride (P(O)Cl$_3$) (0.30 g, 1.9 mmol) and the mixture was stirred overnight at room temperature. The suspension was added to water (10 mL) and toluene (15 mL). The aqueous layer was separated and washed with toluene (10 mL). The combined organic layers were concentrated at 45° C. Two portions of toluene (5 mL each) were added and stripped off to remove any traces of hydrochloric acid.

According to GP6a the following compounds were prepared:

Example 7a

1-{[(4S)-2,2-dimethyl-1,3-dioxolan-4-yl]methyl}cyclopropanesulfonyl chloride (S)-10

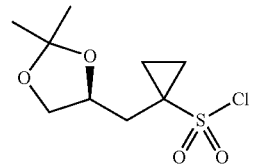

(S)-10 was obtained from (S)-7 in 96.0% yield.
R$_f$: 0.53 (silica gel, n-hexane/ethyl acetate 1:1)
MS (DCI): m/z=255.1 [M+H]$^+$ (100), 223.1 (40), 196.2 (10), 148.2 (4)
$^1$H NMR (400 MHz, Chloroform-d) δ=1.29-1.37 (m, 4H) 1.39 (s, 3H) 1.56-1.65 (m, 1H) 1.70-1.87 (m, 2H) 2.06 (dd, J=15.41, 9.05 Hz, 1H) 2.56-2.67 (m, 1H) 3.59 (dd, J=7.83, 7.09 Hz, 1H) 4.15 (dd, J=8.07, 6.11 Hz, 1H) 4.40 (d, J=6.11 Hz, 1H) ppm

Example 7b

1-{[(4R)-2,2-dimethyl-1,3-dioxolan-4-yl]methyl}cyclopropanesulfonyl chloride (R)-10

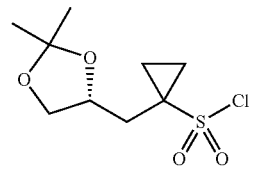

(R)-10 was obtained from (R)-7 in 86.2% yield.
R$_f$: 0.53 (silica gel, n-hexane/ethyl acetate 1:1)

MS (DCI): m/z=255.1 [M+H]$^+$ (100), 223.1 (40), 196.2 (10), 148.2 (4)

$^1$H NMR (400 MHz, Chloroform-d) δ=1.29-1.37 (m, 4H) 1.39 (s, 3H) 1.56-1.65 (m, 1H) 1.70-1.87 (m, 2H) 2.06 (dd, J=15.41, 9.05 Hz, 1H) 2.56-2.67 (m, 1H) 3.59 (dd, J=7.83, 7.09 Hz, 1H) 4.15 (dd, J=8.07, 6.11 Hz, 1H) 4.40 (d, J=6.11 Hz, 1H) ppm GP6b:

To a suspension of 7 (5.0 g, 19.0 mmol) in 36 mL pyridine was added at 60° C. a solution of thionyl chloride (SOCl$_2$) (13.8 g, 116.0 mmol) in toluene (38 mL) over 10 min. The mixture was stirred for 30 min at 60° C. After cooling to room temperature, toluene (75 mL) was added and the reaction suspension was added to cold water (60 mL). The organic layer was separated and washed twice with cold water (60 mL each). The combined organic layers were concentrated at 50° C.

According to GP6b the following compound was prepared:

Example 7c

1-{[(4S)-2,2-dimethyl-1,3-dioxolan-4-yl]methyl}cyclopropanesulfonyl chloride (S)-10

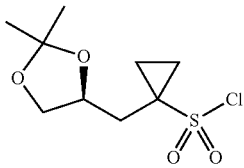

(S)-10 was obtained from (S)-7 in 95.1% yield.

Example 7-Br

General Procedure for the Synthesis of 1-{[2,2-dimethyl-1,3-dioxolan-4-yl]methyl}cyclopropanesulfonyl bromides 10-Br (GP6-Br)

To a suspension of 7 (5.00 g, 19.4 mmol) in 50 mL pyridine was added under cooling phosphoric tribromide (P(O)Br$_3$) (8.33 g, 29.0 mmol) and the mixture was stirred for 1 h at room temperature. The suspension was added to water (100 mL) and toluene (150 mL). The aqueous layer was separated and washed with toluene (100 mL). The combined organic layers were concentrated at 45° C. Two portions of toluene (50 mL each) were added and stripped off to remove any traces of hydrochloric acid.

According to GP6-Br the following compounds were prepared:

Example 7d.1

1-{[(4S)-2,2-dimethyl-1,3-dioxolan-4-yl]methyl}cyclopropanesulfonyl bromide (S)-10-Br

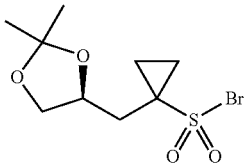

(S)-10-Br was obtained from (S)-7 in 89.8% yield.

R$_f$: 0.53 (silica gel, n-hexane/ethyl acetate 2:1)

MS (DCI): m/z=317.9, 315.9 [M+NH$_4$]$^+$ (20), 301.0, 299.0 [M+H]$^+$ (100), 196.2 (18), 136.1 (46), 130.2 (16), 102.2 (70)

$^1$H NMR (400 MHz, Chloroform-d) δ=1.31-1.43 (m, 1H) 1.34 (s, 3H) 1.40 (s, 3H) 1.61-1.69 (m, 1H) 1.69-1.77 (m, 1H) 1.84 (m, 1H) 2.04 (dd, J=15.41, 9.05 Hz, 1H) 2.57-2.64 (m, 1H) 3.60 (dd, J=8.19, 6.72 Hz, 1H) 4.16 (dd, J=8.31, 6.11 Hz, 1H) 4.39 (dd, J=6.24, 3.06 Hz, 1H) ppm Example 7e 1-{[(4R)-2,2-dimethyl-1,3-dioxolan-4-yl]methyl}cyclopropanesulfonyl bromide (R)-10-Br

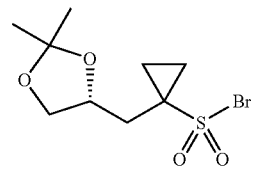

(R)-10-Br was obtained according to GP6-Br from (R)-7 in 86.9% yield.

R$_f$: 0.55 (silica gel, n-hexane/ethyl acetate 2:1)

MS (DCI): m/z=318.0, 316.0 [M+NH$_4$]$^+$ (25), 301.0, 299.0 [M+H]$^+$ (100), 238.2 (20), 221.1 (34), 196.1 (70), 180.1 (20)

$^1$H NMR (400 MHz, Chloroform-d) δ=1.31-1.43 (m, 1H) 1.34 (s, 3H) 1.40 (s, 3H) 1.61-1.69 (m, 1H) 1.69-1.77 (m, 1H) 1.84 (m, 1H) 2.04 (dd, J=15.41, 9.05 Hz, 1H) 2.57-2.64 (m, 1H) 3.60 (dd, J=8.19, 6.72 Hz, 1H) 4.16 (dd, J=8.31, 6.11 Hz, 1H) 4.39 (dd, J=6.24, 3.06 Hz, 1H) ppm Example 8

General Procedure for the Synthesis of 1-{[2,2-dimethyl-1,3-dioxolan-4-yl]methyl}cyclopropanesulfonamides 11 (GP7)

To 10 (0.67 mmol) in dichloromethane (0.35 mL) were added at room temperature lithium bromide (57.9 mg, 0.67 mmol), pyridine (270 μL, 3.3 mmol) and aniline (54.7 μL, 0.6 mmol). The suspension was stirred overnight, dichloromethane (5 mL) was added, the organic layer was washed three times with hydrochloric acid (2.5%, 17 mL each), dried over magnesium sulfate and concentrated to an orange oil.

The enantiomeric purity of 6 was determined by chiral HPLC (CHIRALPAK IB, 5 μm column length 25 cm, internal diameter 4.6 mm; temperature of the column oven 35° C.; eluent n-heptane/ethanol 95:5 v/v; flow rate 1.0 mL/min; detection wavelength 228 nm; retention time (R)-11 approx. 10.6 min, (S)-11 approx. 13.4 min.

According to GP7 the following compounds were prepared:

Example 8a

1-{[(4S)-2,2-dimethyl-1,3-dioxolan-4-yl]methyl}-N-phenylcyclopropanesulfonamide (S)-11

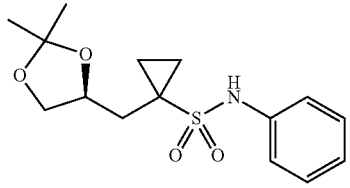 [SMILES: CC1(C)OC[C@H](CC2(S(=O)(=O)Nc3ccccc3)CC2)O1]

(S)-11 was obtained from (S)-10 in 70.0% yield.
$R_f$: 0.48 (silica gel, n-hexane/ethyl acetate 1:1)
MS (DCI): m/z=329.0 [M+NH$_4$]$^+$ (67), 312.2 [M+H]$^+$ (100), 254.1 (35), 223.1 (5).
$^1$H NMR (400 MHz, DMSO-d$_6$) δ=0.80-0.92 (m, 1H) 0.92-1.01 (m, 1H) 1.07 (s, 2H) 1.16-1.24 (m, 3H) 1.26 (s, 3H) 1.89-2.02 (m, 1H) 2.02-2.18 (m, 1H) 3.41 (s, 1H) 3.96 (s, 1H) 4.15-4.31 (m, 1H) 7.09 (s, 1H) 7.18-7.27 (m, 1H) 7.29 (d, J=7.34 Hz, 2H) 9.80 (br. s, 1H) ppm

Example 8b

1-{[(4R)-2,2-dimethyl-1,3-dioxolan-4-yl]methyl}-N-phenylcyclopropanesulfonamide (R)-11

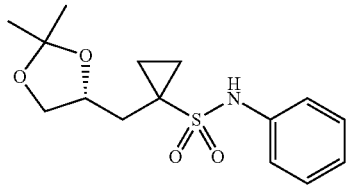 [SMILES: CC1(C)OC[C@@H](CC2(S(=O)(=O)Nc3ccccc3)CC2)O1]

(R)-11 was obtained from (R)-10 in 81.9% yield.
$R_f$: 0.48 (silica gel, n-hexane/ethyl acetate 1:1)
MS (DCI): m/z=329.0 [M+NH$_4$]$^+$ (67), 312.2 [M+H]$^+$ (100), 254.1 (35), 223.1 (5).
$^1$H NMR (400 MHz, DMSO-d$_6$) δ=0.80-0.92 (m, 1H) 0.92-1.01 (m, 1H) 1.07 (s, 2H) 1.16-1.24 (m, 3H) 1.26 (s, 3H) 1.89-2.02 (m, 1H) 2.02-2.18 (m, 1H) 3.41 (s, 1H) 3.96 (s, 1H) 4.15-4.31 (m, 1H) 7.09 (s, 1H) 7.18-7.27 (m, 1H) 7.29 (d, J=7.34 Hz, 2H) 9.80 (br. s, 1H) ppm

Example 9a

Synthesis of N-{3,4-difluoro-2-[(2-fluoro-4-iodophenyl)amino]-6-methoxyphenyl}-1-{[(4S)-2,2-dimethyl-1,3-dioxolan-4-yl]methyl}cyclopropanesulfonamide (S)-13

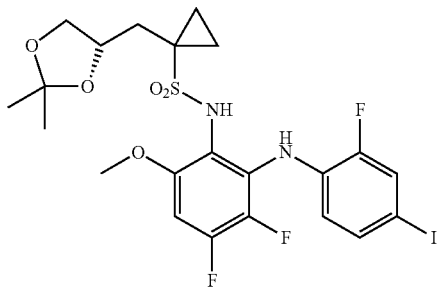

To a mixture of 5,6-difluoro-N1-(4-fluoro-2-iodophenyl)-3-methoxybenzene-1,2-diamine [ref. 2, Example 50, Step B] (0.9 g, 2.3 mmol) and tetrabutylammonium bromide (0.74 g, 2.3 mmol) in pyridine (0.76 mL) and sulfolane (1.5 mL) was added (S)-10 (0.8 g, 3.0 mmol). It was stirred at 70° C. for 18 h. It was diluted with ethyl acetate (20 mL) and hydrochloric acid (10%, 5 mL). The organic layer was separated, washed with sat. aq. sodium hydrogen carbonate (20 mL), and with water (10 mL). The organic layer was dried over magnesium sulfate and concentrated to a solid. The solid was purified by chromatography (silica gel, hexane/ethyl acetate 1:1).

Yield: 1.3 g, 92.2%

$R_f$=0.46 (silica gel hexanes/ethyl acetate 1:1)

MS (DCI): m/z=613.3 [M+H]$^+$ (100), 555.2 (30), 459.1 (20), 393.0 (45) 267.1 (10), 219.0 (5)

$^1$H NMR (400 MHz, DMSO-d$_6$) δ=0.82-1.02 (m, 4H) 1.24 (s, 3H) 1.29 (s, 3H) 2.07 (dd, J=15.28, 7.70 Hz, 1H) 2.35 (dd, J=15.28, 4.52 Hz, 1H) 3.46 (t, J=7.70 Hz, 1H) 3.83 (s, 3H) 4.03 (m, J=7.34 Hz, 2H) 4.19-4.29 (m, 1H) 6.48 (td, J=8.80, 4.65 Hz, 1H) 7.07 (dd, J=12.59, 7.21 Hz, 1H) 7.33 (d, J=8.56 Hz, 1H) 7.36-7.41 (br. s, 1H) 7.56 (dd, J=10.76, 1.71 Hz, 1H) 9.14 (s, 1H) ppm (S)-13 was obtained from (S)-10-Br in 100.0% yield To a mixture of 5,6-difluoro-N1-(4-fluoro-2-iodophenyl)-3-methoxybenzene-1,2-diamine [ref. 2, Example 50, Step B] (0.9 g, 2.3 mmol) in pyridine (0.76 mL) and sulfolane (1.5 mL) was added (S)-10-Br (0.94 g, 3.0 mmol). It was stirred at 23° C. for 18 h. It was diluted with ethyl acetate (20 mL) and hydrochloric acid (10%, 5 mL). The organic layer was separated, washed with sat. aq. sodium hydrogen carbonate (20 mL), and with water (10 mL). The organic layer was dried over magnesium sulfate and concentrated to a solid. The solid was purified by chromatography (silica gel, hexane/ethyl acetate 1:1).

Yield: 1.4 g, 100.0%

Example 9b

Synthesis of N-{3,4-difluoro-2-[(2-fluoro-4-iodophenyl)amino]-6-methoxyphenyl}-1-{[(4R)-2,2-dimethyl-1,3-dioxolan-4-yl]methyl}cyclopropanesulfonamide (R)-13

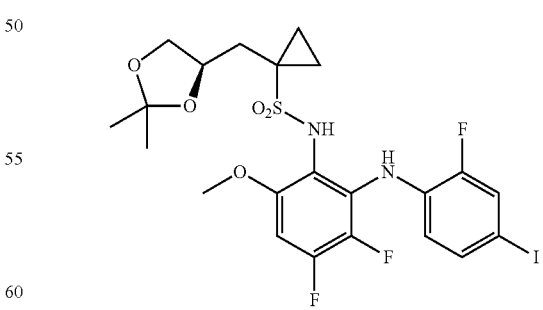

A mixture of (R)-10 (400 mg, 1.57 mmol), 5,6-difluoro-N1-(4-fluoro-2-iodophenyl)-3-methoxybenzene-1,2-diamine (618 mg, 1.57 mmol) and 4-dimethyl aminopyridine (38 mg, 0.31 mmol) in pyridine (5 mL) was stirred at 50° C. for 45 h. The solvent was stripped off in vacuum and the residue purified by chromatography (silica gel 1. dichloromethane, 2. methanol) to give 820 mg of crude product.

$R_f$=0.28 (silica gel, dichloromethane)

The crude product was purified by a second chromatography (silica gel, hexanes/ethyl acetate 1:1).

Yield: 350 mg 38.9%

$R_f$=0.46 (silica gel, hexanes/ethyl acetate 1:1)

MS (DCI): m/z=613.3 [M+H]$^+$ (100), 555.2 (30), 459.1 (20), 393.0 (45) 267.1 (10), 219.0 (5)

$^1$H NMR (400 MHz, DMSO-$d_6$) δ=0.82-1.02 (m, 4H) 1.24 (s, 3H) 1.29 (s, 3H) 2.07 (dd, J=15.28, 7.70 Hz, 1H) 2.35 (dd, J=15.28, 4.52 Hz, 1H) 3.46 (t, J=7.70 Hz, 1H) 3.83 (s, 3H) 4.03 (m, J=7.34 Hz, 2H) 4.19-4.29 (m, 1H) 6.48 (td, J=8.80, 4.65 Hz, 1H) 7.07 (dd, J=12.59, 7.21 Hz, 1H) 7.33 (d, J=8.56 Hz, 1H) 7.36-7.41 (br. s, 1H) 7.56 (dd, J=10.76, 1.71 Hz, 1H) 9.14 (s, 1H) ppm Example 10a.1

Synthesis of N-{3,4-difluoro-2-[(2-fluoro-4-iodophenyl)amino]-6-methoxyphenyl}-1-[(2S)-2,3-dihydroxy-propyl]cyclopropanesulfonamide (S)-14

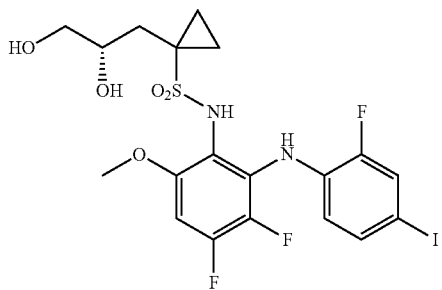 [SMILES: COc1cc(F)c(F)c(Nc2ccc(I)cc2F)c1NS(=O)(=O)C1(C[C@H](O)CO)CC1]

To a mixture of 5,6-difluoro-N1-(4-fluoro-2-iodophenyl)-3-methoxybenzene-1,2-diamine [ref. 2, Example 50, Step B] (0.9 g, 2.3 mmol) and tetrabutylammonium bromide (TBAB) (0.74 g, 2.3 mmol) in pyridine (0.76 mL) and sulfolane (1.5 mL) was added (S)-10 (0.8 g, 3.0 mmol). It was stirred at 70° C. for 18 h to achieve complete conversion to (S)-13. The reaction mixture was stirred with hydrochloric acid (10%, 4 mL) for 1 h. It was diluted with ethyl acetate (20 mL), the organic layer was washed two times with water (30 mL, 2×15 mL), dried over magnesium sulfate and concentrated to a solid. The solid was purified by chromatography (silica gel, ethyl acetate).

Yield: 1.2 g, 91.6%

$R_f$: 0.12 (silica gel, ethyl acetate)

MS (DCI): m/z 590.1 [M+NH$_4$]$^+$ (40), 573.0 [M+H]$^+$ (28), 395.0 (76), 372.9 (18), 269.0 (100), 247.0 (25), 130.0 (20), 114.0 (16)

$^1$H NMR (400 MHz, DMSO-$d_6$) δ=0.88-1.04 (m, 4H) 1.79 (dd, J=14.98, 9.41 Hz, 1H) 2.32 (dd, J=14.92, 2.38 Hz, 1H) 3.21-3.37 (m, 2H) 3.56-3.66 (m, 1H) 3.83 (s, 3H) 4.50 (d, J=5.32 Hz, 1H) 4.57 (t, J=5.53 Hz, 1H) 6.49 (td, J=8.85, 4.55 Hz, 1H) 7.03 (dd, J=12.62, 7.24 Hz, 1H) 7.34 (d, J=9.29 Hz, 1H) 7.45 (br. s, 1H) 7.56 (dd, J=10.91, 1.86 Hz, 1H) 9.04 (br. s, 1H) ppm Optical purity: >99.9% ee (S)-14 was obtained from (S)-13 which was prepared from (S)-10-Br A mixture of (S)-13 (1.3 g, 2.1 mmol) in pyridine (0.76 mL), sulfolane (1.5 mL) and hydrochloric acid (10%, 4 mL) was stirred for 1.5 h. It was diluted with ethyl acetate (20 mL) and water (30 mL), the organic layer was washed two times with water (30 mL, 2×15 mL), dried over magnesium sulfate and concentrated to a solid. The solid was purified by chromatography (silica gel, ethyl acetate).

Yield: 1.1 g, 91.6%

$R_f$: 0.12 (silica gel, ethyl acetate)

MS (DCI): m/z 590.1 [M+NH$_4$]$^+$ (40), 573.0 [M+H]$^+$ (28), 395.0 (76), 372.9 (18), 269.0 (100), 247.0 (25), 130.0 (20), 114.0 (16)

$^1$H NMR (400 MHz, DMSO-$d_6$) δ=0.88-1.04 (m, 4H) 1.79 (dd, J=14.98, 9.41 Hz, 1H) 2.32 (dd, J=14.92, 2.38 Hz, 1H) 3.21-3.37 (m, 2H) 3.56-3.66 (m, 1H) 3.83 (s, 3H) 4.50 (d, J=5.32 Hz, 1H) 4.57 (t, J=5.53 Hz, 1H) 6.49 (td, J=8.85, 4.55 Hz, 1H) 7.03 (dd, J=12.62, 7.24 Hz, 1H) 7.34 (d, J=9.29 Hz, 1H) 7.45 (br. s, 1H) 7.56 (dd, J=10.91, 1.86 Hz, 1H) 9.04 (br. s, 1H) ppm Optical purity: >99.5% ee Example 10b N-{3,4-difluoro-2-[2-fluoro-4-iodophenyl)amino]-6-methoxyphenyl}-1-[(2R)-2,3-dihydroxy-propyl]cyclopropanesulfonamide (R)-14

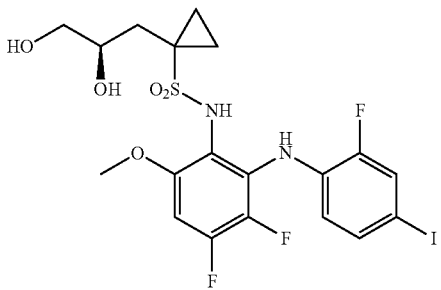 [SMILES: COc1cc(F)c(F)c(Nc2ccc(I)cc2F)c1NS(=O)(=O)C1(C[C@@H](O)CO)CC1]

A solution of (R)-13 (120 mg, 0.6 mmol) in tetrahydrofuran (2.5 mL) and hydrochloric acid (10%, 2 mL) was stirred at room temperature until TLC (silica gel, ethyl acetate) indicated complete conversion (2 h). Ethyl acetate (2.5 mL) and a saturated aq. solution of sodium hydrogen carbonate (2.5 mL) were added, the aqueous layer was extracted with ethyl acetate (2.0 mL), the combined organic layer was washed with water (2×2 mL), dried over magnesium sulfate and concentrated to a solid. The solid was purified by chromatography (silica gel 1. ethyl acetate, 2. ethyl acetate/methanol 10:1).

Yield: 61 mg 54.4%

$R_f$: 0.12 (silica gel, ethyl acetate)

MS (DCI): m/z 590.1 [M+NH$_4$]$^+$ (40), 573.0 [M+H]$^+$ (28), 395.0 (76), 372.9 (18), 269.0 (100), 247.0 (25), 130.0 (20), 114.0 (16)

$^1$H NMR (400 MHz, DMSO-$d_6$) δ=0.88-1.04 (m, 4H) 1.79 (dd, J=14.98, 9.41 Hz, 1H) 2.32 (dd, J=14.92, 2.38 Hz, 1H) 3.21-3.37 (m, 2H) 3.56-3.66 (m, 1H) 3.83 (s, 3H) 4.50 (d, J=5.32 Hz, 1H) 4.57 (t, J=5.53 Hz, 1H) 6.49 (td, J=8.85, 4.55 Hz, 1H) 7.03 (dd, J=12.62, 7.24 Hz, 1H) 7.34 (d, J=9.29 Hz, 1H) 7.45 (br. s, 1H) 7.56 (dd, J=10.91, 1.86 Hz, 1H) 9.04 (br. s, 1H) ppm Optical purity: >99.9% ee (R)-14 was obtained from (R)-10-Br To a mixture of 5,6-difluoro-N1-(4-fluoro-2-iodophenyl)-3-methoxybenzene-1,2-diamine [ref. 2, Example 50, Step B] (0.8 g, 2.0 mmol) in pyridine (0.68 mL) and sulfolane (1.3 mL) was added (R)-10-Br (0.7 g, 2.4 mmol). It was stirred at 23° C. for 18 h to achieve complete conversion to (R)-13. The reaction mixture was stirred with hydrochloric acid (10%, 6 mL) for 1.5 h. It was diluted with ethyl acetate (20 mL) and water (30 mL), the organic layer was washed two times with water (30 mL, 2×15 mL), dried over magnesium sulfate and concentrated to a solid. The solid was purified by chromatography (silica gel, ethyl acetate).

Yield: 1.1 g, 90.5%

$R_f$: 0.12 (silica gel, ethyl acetate)

MS (DCI): m/z 590.1 [M+NH$_4$]$^+$ (40), 573.0 [M+H]$^+$ (28), 395.0 (76), 372.9 (18), 269.0 (100), 247.0 (25), 130.0 (20), 114.0 (16)

$^1$H NMR (400 MHz, DMSO-d$_6$) δ=0.88-1.04 (m, 4H) 1.79 (dd, J=14.98, 9.41 Hz, 1H) 2.32 (dd, J=14.92, 2.38 Hz, 1H) 3.21-3.37 (m, 2H) 3.56-3.66 (m, 1H) 3.83 (s, 3H) 4.50 (d, J=5.32 Hz, 1H) 4.57 (t, J=5.53 Hz, 1H) 6.49 (td, J=8.85, 4.55 Hz, 1H) 7.03 (dd, J=12.62, 7.24 Hz, 1H) 7.34 (d, J=9.29 Hz, 1H) 7.45 (br. s, 1H) 7.56 (dd, J=10.91, 1.86 Hz, 1H) 9.04 (br. s, 1H) ppm Optical purity: >99.6% ee The enantiomeric purity of 14 was determined by chiral HPLC (CHIRALPAK AD-H, 5 μm column length 25 cm, internal diameter 4.6 mm; temperature of the column oven 35° C.; eluent n-heptane/isopropanol 8:2 v/v; flow rate 1.5 mL/min; detection wavelength 300 nm; retention time (S)-14 approx. 10 min, (R)-14 approx. 16 min.

REFERENCES

[1] C. Iverson, G. Larson, C. Lai, L.-T. Yeh, C. Dadson, P. Weingarten, T. Appleby, T. Vo, A. Maderna, J.-M. Vernier; R. Hamatake, J. N. Miner, B. Quart, Cancer Res. 2009, 69, 6839-6847

[2] U.S. patent application published under 2008/0058340

[3] PCT patent application published under WO 2010/145197 A1

[4] S. Fujita, Synthesis 1982, 423

[5] G. Blotny, Tetrahedron Lett. 2003, 44, 1499-1501

[6] J. Huang, T. S. Widlanski, Tetrahedron Lett. 1992, 33, 2657-2660

[7] PCT patent application published under WO 2011/009541 A1

The invention claimed is:

1. The compound
1-{[(4S)-2,2-dimethyl-1,3-dioxolan-4-yl]methyl}cyclopropanesulfonyl bromide (S)-10-Br:

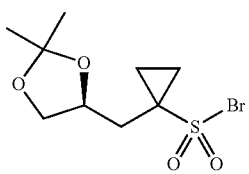

2. A method of preparing a compound of formula (S)-14:

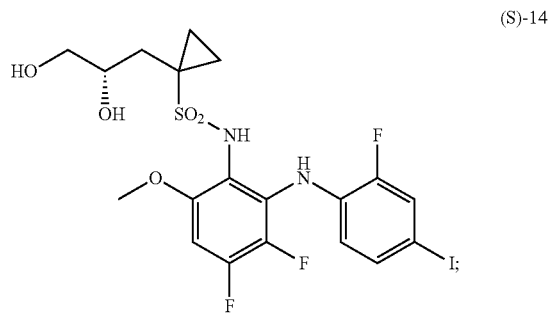 [SMILES: COc1cc(F)c(F)c(Nc2ccc(I)cc2F)c1NS(=O)(=O)C1(C[C@H](O)CO)CC1]

comprising:

i) reacting a compound of formula (S)-10:

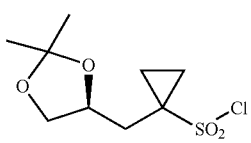

with a compound of formula (12):

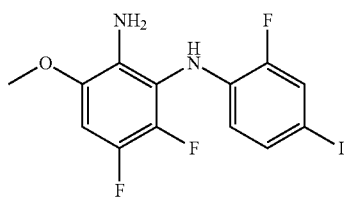

in the presence of a bromide, optionally in the presence of a base, and optionally in a solvent, thereby providing a reaction mixture containing a compound of formula (S)-13:

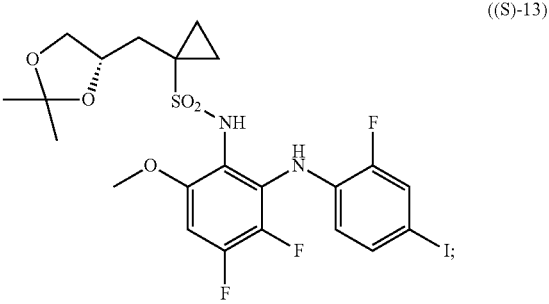

and, then, ii) adding an aqueous mineral acid to said reaction mixture containing a compound of formula (S)-13, thereby providing a compound of formula (S)-14.

3. A method of preparing a compound of formula (S)-14:

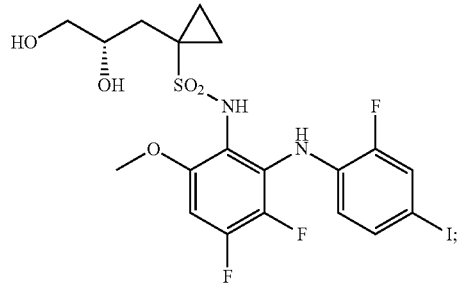

comprising:
i) reacting a compound of formula (S)-10-Br:

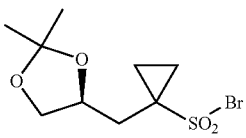

with a compound of formula (12):

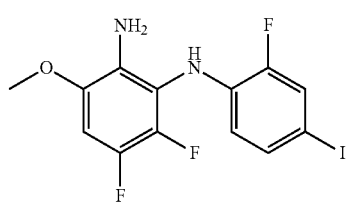

optionally in the presence of a base, and optionally in a solvent,
thereby providing a reaction mixture containing a compound of formula (S)-13:

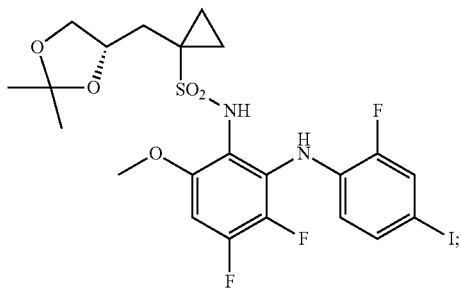

and, then,
ii) adding an aqueous mineral acid to said reaction mixture containing a compound of formula (S)-13,
thereby providing a compound of formula (S)-14.

4. The method according to claim 2, wherein said compound of formula (S)-10:

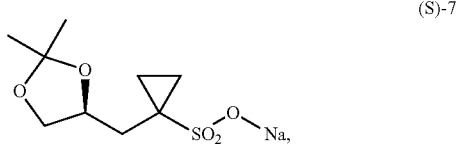

is prepared by reacting a compound of formula (S)-7:

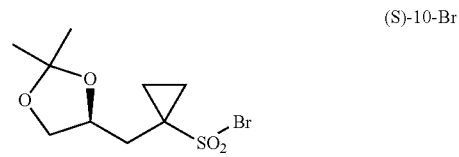

with a chlorinating agent, optionally in a solvent, thereby providing a compound of formula (S)-10.

5. The method according to claim 3, wherein said compound of formula (S)-10-Br:

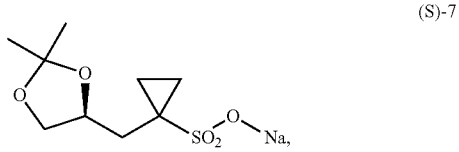

is prepared by reacting a compound of formula (S)-7:

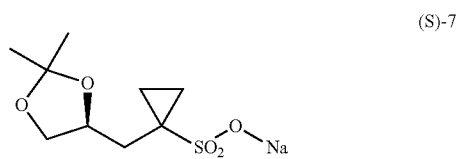

with a brominating agent, optionally in a solvent, thereby providing a compound of formula (S)-10-Br.

6. The method of claim 4, wherein said compound of formula (S)-7:

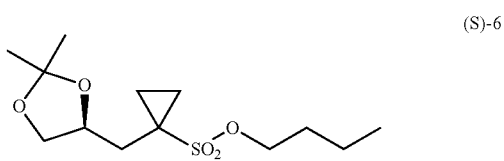 [SMILES: CCCCOS(=O)(=O)C1(C[C@H]2COC(C)(C)O2)CC1]

is prepared by reacting a compound of formula (S)-6:

with a sodium alkoxide, optionally in a solvent, thereby providing a compound of formula (S)-7.

7. The method of claim 6, wherein said compound of formula (S)-6:

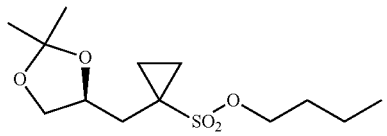
(S)-6 is prepared by reacting a compound of formula (S)-4:

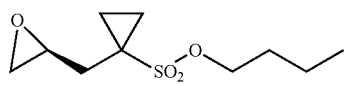
(S)-4 with either:
a) boron trifluoride, optionally in the form of a complex, optionally in a solvent, or
b) phosphomolybdic acid hydrate, optionally in a solvent,
thereby providing a compound of formula (S)-6.

8. The method of claim 7, wherein said compound of formula (S)-4:

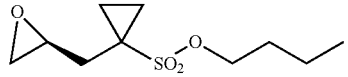
(S)-4 is prepared by reacting a compound of formula (S)-3:

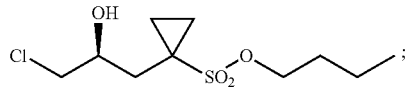
(S)-3 with a base, optionally in a solvent,
thereby providing a compound of formula (S)-4.

9. The method of claim 8, wherein said compound of formula (S)-3:

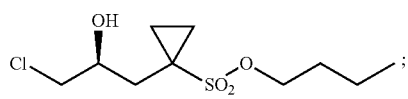
(S)-3 is prepared by:
a) reacting a compound of formula 2:

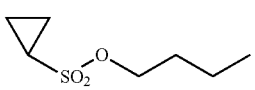
(2)

with a base to form a deprotonated compound of formula 2, optionally in a solvent, b) adding a compound of formula (S)-1 and boron trifluoride, optionally in the form of a complex; and
c) allowing the deprotonated compound of formula 2 to react with the compound of formula (S)-1:

(S)-1 thereby providing a compound of formula (S)-3.

10. The method of claim 6, wherein said compound of formula (S)-6:

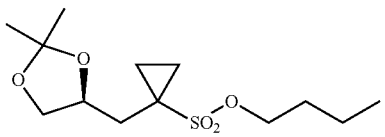
(S)-6 is prepared by reacting a compound of formula (S)-5:

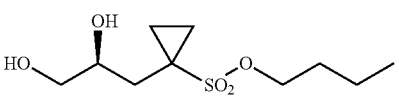
(S)-5 with 2,2-dimethoxypropane, optionally in a solvent, and optionally in the presence of a catalyst,
thereby providing a compound of formula (S)-6.

11. The method of claim 10, wherein said compound of formula (S)-5:

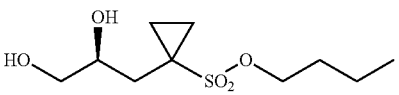
(S)-5 is prepared by reacting a compound of formula (S)-9:

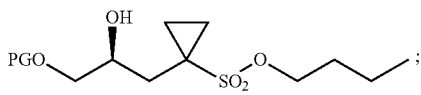
(S)-9 wherein PG represents a protecting group, with an acid, optionally in a solvent,
thereby providing a compound of formula (S)-5.

12. The method of claim 11, wherein said compound of formula (S)-9:

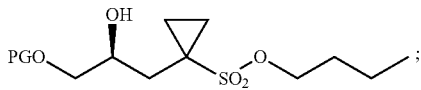
(S)-9 wherein PG represents a t-butyldimethylsilyl- group or a tetrahydropyranyl group, is prepared by:
a) reacting a compound of formula 2:

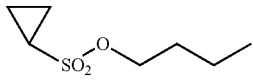
(2)

with a base to form a deprotonated compound of formula 2, optionally in a solvent,
b) adding a compound of formula (S)-8 and boron trifluoride, optionally in the form of a complex; and
c) allowing the deprotonated compound of formula 2 to react with the compound of formula (S)-8:

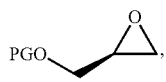
(S)-8 wherein PG represents a t-butyldimethylsilyl- group or a tetrahydropyranyl group thereby providing a compound of formula (S)-9.

13. The method of claim 5, wherein said compound of formula (S)-7:

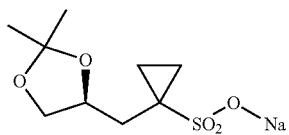
(S)-7 is prepared by reacting a compound of formula (S)-6:

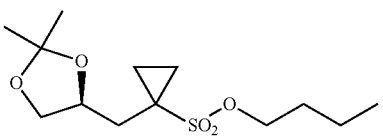
(S)-6 with a sodium alkoxide, optionally in a solvent, thereby providing a compound of formula (S)-7.

* * * * *